US011471168B2

(12) United States Patent
Lark et al.

(10) Patent No.: US 11,471,168 B2
(45) Date of Patent: Oct. 18, 2022

(54) MEDICAL DEVICES AND RELATED METHODS FOR TRANSFORMING BONE, OTHER TISSUE, OR MATERIAL

(71) Applicants: Robert K. Lark, Chapel Hill, NC (US); Edward C. Skolnick, Denville, NJ (US); Antoine R. Kaeslin, Bethel, CT (US)

(72) Inventors: Robert K. Lark, Chapel Hill, NC (US); Edward C. Skolnick, Denville, NJ (US); Antoine R. Kaeslin, Bethel, CT (US)

(73) Assignee: Innovations 4 Surgery, LLC, Chapel Hill, NC (US)

( * ) Notice: Subject to any disclaimer, the term of this patent is extended or adjusted under 35 U.S.C. 154(b) by 26 days.

(21) Appl. No.: 17/128,098

(22) Filed: Dec. 19, 2020

(65) Prior Publication Data
US 2021/0186525 A1    Jun. 24, 2021

Related U.S. Application Data

(60) Provisional application No. 62/951,389, filed on Dec. 20, 2019.

(51) Int. Cl.
| | | |
|---|---|---|
| *A61B 17/14* | (2006.01) | |
| *A61B 17/34* | (2006.01) | |
| *A61B 17/16* | (2006.01) | |
| *A61B 17/32* | (2006.01) | |

(52) U.S. Cl.
CPC ........ *A61B 17/142* (2016.11); *A61B 17/1615* (2013.01); *A61B 17/1628* (2013.01); *A61B 17/320068* (2013.01)

(58) Field of Classification Search
CPC ....... A61B 17/14; A61B 17/142; A61B 17/32; A61B 17/320068; A61B 2017/320074; A61B 2017/320075; A61B 2017/320082; A61B 2017/320088
See application file for complete search history.

(56) References Cited

U.S. PATENT DOCUMENTS

| | | | | |
|---|---|---|---|---|
| 5,261,922 A | * | 11/1993 | Hood ............. | A61B 17/320068 D24/146 |
| 5,728,130 A | * | 3/1998 | Ishikawa ............ | A61B 17/3476 604/264 |
| 6,379,371 B1 | * | 4/2002 | Novak ........... | A61B 17/320068 30/123.3 |
| 6,443,969 B1 | * | 9/2002 | Novak ........... | A61B 17/320068 606/169 |
| 8,343,178 B2 | * | 1/2013 | Novak ........... | A61B 17/320068 606/169 |
| D680,218 S | * | 4/2013 | Darian ........................ | D24/146 |

(Continued)

*Primary Examiner* — Eric S Gibson
(74) *Attorney, Agent, or Firm* — Olive Law Group, PLLC

(57) ABSTRACT

Medical devices and related methods for transforming bone, other tissue, or other material are disclosed herein. According to an aspect, a cutting device includes a static casing that defines a sheathing slot and an opening. The sheathing slot extends to the opening and has a first height at an end of the opening. Further, the bone cutting device includes a horn including a first end and a second end. The first end is configured to operatively connect to a source of movement. Further, the second end includes a cutting component having a second height. The first height is greater than the second height.

16 Claims, 28 Drawing Sheets

(56) References Cited

U.S. PATENT DOCUMENTS

| | | | | |
|---|---|---|---|---|
| 9,320,528 | B2* | 4/2016 | Voic | A61B 17/16 |
| 9,554,809 | B2* | 1/2017 | Lark | A61B 17/1613 |
| 10,238,415 | B2* | 3/2019 | Naono | A61B 17/320068 |
| 10,702,296 | B2* | 7/2020 | Boudreaux | A61B 17/320068 |
| 2003/0204199 | A1* | 10/2003 | Novak | A61B 17/320068 606/169 |
| 2005/0273127 | A1* | 12/2005 | Novak | A61B 17/320068 606/169 |
| 2008/0009848 | A1* | 1/2008 | Paraschiv | A61B 17/142 606/34 |
| 2013/0204285 | A1* | 8/2013 | Gouery | A61B 17/320068 606/169 |
| 2015/0005771 | A1* | 1/2015 | Voic | A61B 17/14 606/79 |
| 2015/0088137 | A1* | 3/2015 | Manna | A61B 17/142 606/79 |
| 2016/0089155 | A1* | 3/2016 | Lark | A61B 17/1613 606/169 |
| 2017/0056052 | A1* | 3/2017 | Dickerson | A61B 17/320068 |
| 2017/0340339 | A1* | 11/2017 | Madan | A61B 17/320068 |
| 2017/0340344 | A1* | 11/2017 | Boudreaux | A61B 17/320068 |
| 2017/0340345 | A1* | 11/2017 | Yates | A61B 17/320068 |
| 2018/0344346 | A1* | 12/2018 | Naono | A61B 17/320016 |
| 2021/0121195 | A1* | 4/2021 | Richards | A61B 17/32002 |
| 2021/0186525 | A1* | 6/2021 | Lark | A61B 17/320068 |

\* cited by examiner

MEDICAL DEVICES AND RELATED METHODS FOR TRANSFORMING BONE, OTHER TISSUE, OR MATERIAL

CROSS REFERENCE TO RELATED APPLICATION

This application claims priority to U.S. Provisional Patent Application No. 62/951,389, filed on Dec. 20, 2019 and titled MEDICAL DEVICES AND RELATED METHODS FOR TRANSFORMING BONE, OTHER TISSUE, OR MATERIAL, the disclosure of which is incorporated herein by reference in its entirety.

TECHNICAL FIELD

The presently disclosed subject matter relates generally to medical devices. Particularly, the presently disclosed subject matter relates to medical devices and related methods for transforming bone, other tissue, or material.

BACKGROUND

Traditional surgical saws, such as oscillating saws and reciprocating saws, allow users to cut bones (i.e. perform osteotomies) of relatively large diameters, such as the tibia and femur. These types of surgical saws, however, which are similar in many ways to the toothed saws used to cut wood, metal, and plastic, have significant disadvantages with respect to a patient's well-being. Because surgical saws utilize rapid motion of the saw blade to cut biological tissues, such as bone and cartilage, a significant amount of heat is generated along the blade and particularly at the blade and bone interface. This can be harmful to the patient since prolonged exposure of bone cells to temperatures at or in excess of 47° C. leads to necrosis of those osteocytes. Another disadvantage of these oscillating and reciprocating bone saws is that they produce uneven cuts, preventing ideal realignment and reduction of the osteotomy gap, which is detrimental to efficient healing of the bone. Oscillating and, in particular, reciprocating bone saws, which utilize a number of sharpened teeth along their cutting edges, can tear neighboring soft tissues that are inadvertently caught in the serrations of the rapidly moving blade. Tearing of these soft tissues leads to significant blood loss and potential nerve damage, which undoubtedly hampers the health of the patient.

Traditional oscillating and reciprocating bone saws have employed a variety of different measures to address these disadvantages. With respect to the generation of excessive heat, these surgical saws can utilize irrigation systems to flush the surgical site near the blade and bone interface. These irrigation systems can be separate, requiring an additional device at the surgical site, or integrated. Although effective at flushing a surgical site of unwanted sources of added friction, these irrigation systems are relatively ineffective at actually cooling the blade at the blade and bone interface. For example, one design for a surgical saw that incorporates a means for irrigation comprises a channel between otherwise parallel portions of a saw blade through which fluid can flow out into the surgical site (See U.S. Pat. No. 5,087,261). This channel, though, can be easily compacted with surgical debris, rendering the integrated irrigation system unusable. In addition, providing a channel between parallel portions of the saw blade necessarily increases the likelihood of a wider, more uneven cut. Other designs for an oscillating bone saw include outlets along the blade's edge to facilitate irrigation along the blade and bone interface (See U.S. Pat. Nos. 4,008,720 and 5,122,142). However, these channels can be similarly compacted with surgical debris, rendering them useless. More so, channels along the very blade edge result in a blade edge that is not continuous, which reduces the cutting efficiency of the blade. Despite any potential efficacy in flushing a site of surgical debris, these systems do very little to actually cool the very blade edge, specifically at the blade and bone interface.

Just as with saws used to cut wood, metal, and plastic, a user can avoid rough or uneven cuts by using a saw blade that incorporates more teeth along the edge of the blade and/or teeth having differing angles. While this can produce a relatively finer cut, the resulting cut still leaves much to be desired in terms of producing smooth, even bone surfaces. Cutting guides, which help to stabilize the blade and keep it on a prescribed plane, are often utilized during an osteotomy to improve the precision of the cut. Still, the improvement is not substantial enough to consider these measures a long-term solution with respect to producing smooth bone cuts. In fact, adding teeth or guiding the blade edge have little effect in preventing inadvertent tearing of neighboring soft tissues. Although efforts are taken to protect soft tissues from damage and prevent significant blood loss, the inherently close confines typical in performing any osteotomy make it extremely difficult to completely eliminate such damage, especially to those tissues that are unseen or positioned beneath the bone being cut. This is compounded by the fact that the saw blades used with many oscillating and reciprocating bone saws are relatively large.

A variety of ultrasonic surgical devices are now utilized in a number of surgical procedures, including surgical blades that are capable of cutting biological tissues such as bone and cartilage. These types of saw blades are powered by high-frequency and high-amplitude sound waves, consequent vibrational energy being concentrated at the blade's edge by way of an ultrasonic horn. Being powered by sound waves, neighboring soft tissues are not damaged by these types of blades because the blade's edge effectively rebounds due to the elasticity of the soft tissue. Thus, the significant blood loss common with use of traditional bone saws is prevented. In addition, significantly more precise cuts are possible using ultrasonic bone cutting devices, in part, because the blade's edge does not require serrations. Instead, a continuous and sharpened edge, similar to that of a typical scalpel, enables a user to better manipulate the surgical device without the deflection caused by serrations, which is common when using oscillating and reciprocating bone saws. Although ultrasonic cutting blades are advantageous in that they are less likely to tear neighboring soft tissues and more likely to produce relatively more even cuts, these types of blades still generate considerable amounts of heat.

As with traditional bone saws, separate or integrated irrigation systems are often utilized in order to flush the surgical site and generally provide some measure of cooling effect to the blade. However, many of these blades suffer from the same disadvantages as traditional bone saws that have tried to incorporate similar measures. For example, providing openings along the blade's edge through which fluid flows introduces voids in the cutting edge, thereby inhibiting the cutting efficiency of the blade (See U.S. Pat. No. 5,188,102). In addition, these fluid openings can be readily compacted with surgical debris, rendering them useless for their intended function. In other blade designs, the continuity of the blade is maintained and a fluid outlet is positioned just before the blade's edge (See U.S. Pat. No. 8,348,880). However, this fluid outlet merely irrigates the surgical site since it is positioned too far from the blade and bone interface to actually provide the necessary cooling effect. Also, it irrigates only one side of the blade. Another design for an ultrasonic cutting device, which claims to cool the blade, incorporates an irrigation output located centrally along the longitudinal axis of the blade (See U.S. Pat. No. 6,379,371). A recess in the center of the blade tip allows fluid to flow out of this output and toward the blade's edge, flow that is propelled by a source of pressure. However, the positioning of this irrigation output within the contour of the blade tip results in a bifurcation or splitting of the irrigation flow, such splitting tending to distribute fluid at an angle away from the blade's edge. Mentioned above, the excessive heat generated using any cutting blade, including an ultrasonic cutting blade, is focused most significantly at the blade and bone interface. This example for an ultrasonic blade with cooling capabilities, then, does little to actually cool the blade at the blade and bone interface, but instead serves merely to flush debris from the surgical site. Furthermore, this ultrasonic blade is not well-suited to cutting large cross-sections of bone and is used almost exclusively in oral or maxillofacial surgeries, which involve cutting of small bones.

Even assuming that any of the irrigation systems incorporated into the various bone saws provide some measure of cooling, thermal burning of both neighboring soft tissues and bone surfaces remains a significant problem. Because the shaft of the blade also vibrates at a very high frequency, considerable heat is generated along its length, too. The vibrating shaft contacts neighboring soft tissues, potentially burning them. With respect to an osteotomy, as the blade passes through the cross-section of bone, the freshly-cut bone surfaces remain in constant and direct contact with the rapidly vibrating shaft of the blade. As a result, it is not uncommon to burn the bone, produce smoke and, more importantly, kill osteocytes. In fact, simply lengthening an ultrasonic blade to accommodate large cross-sections of bone tissue, for example, increases the surface area through which heat can transfer and, thus, is avoided by manufacturers of these types of blades. While irrigation directed specifically toward the blade's leading edge may provide some measure of cooling at the blade and bone interface, irrigation alone is insufficient in trying to avoid prolonged exposure of bone tissue, for example, to temperatures in excess of 47° C. Therefore, there remains a need for an ultrasonic surgical device that is capable of cutting bones with large cross-sections, such as the femur, while maintaining a working temperature along the entirety of the blade shaft that does not inhibit proper healing of the bone tissue.

BRIEF DESCRIPTION OF THE DRAWINGS

Figure 1:
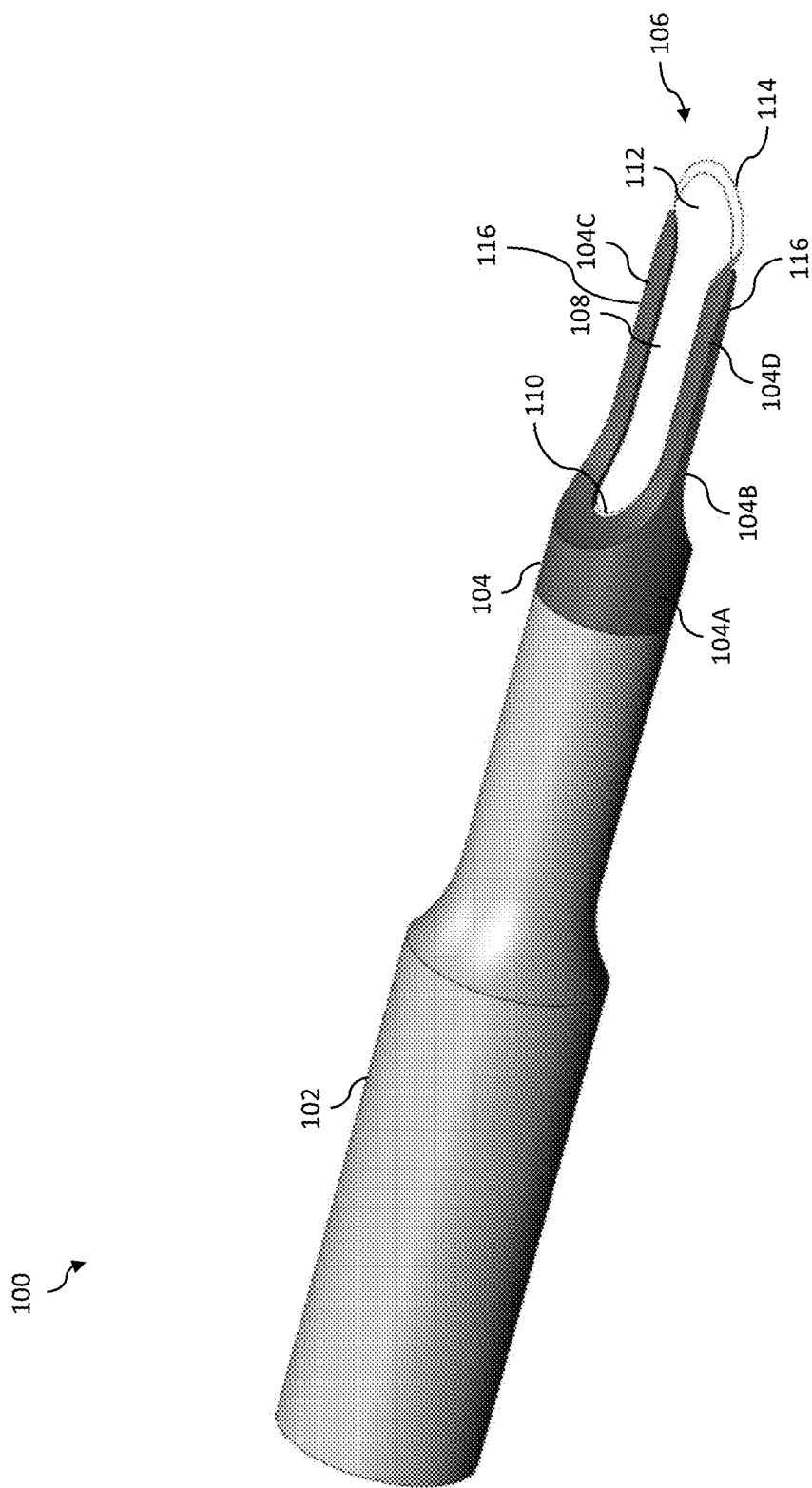
Figure 2:
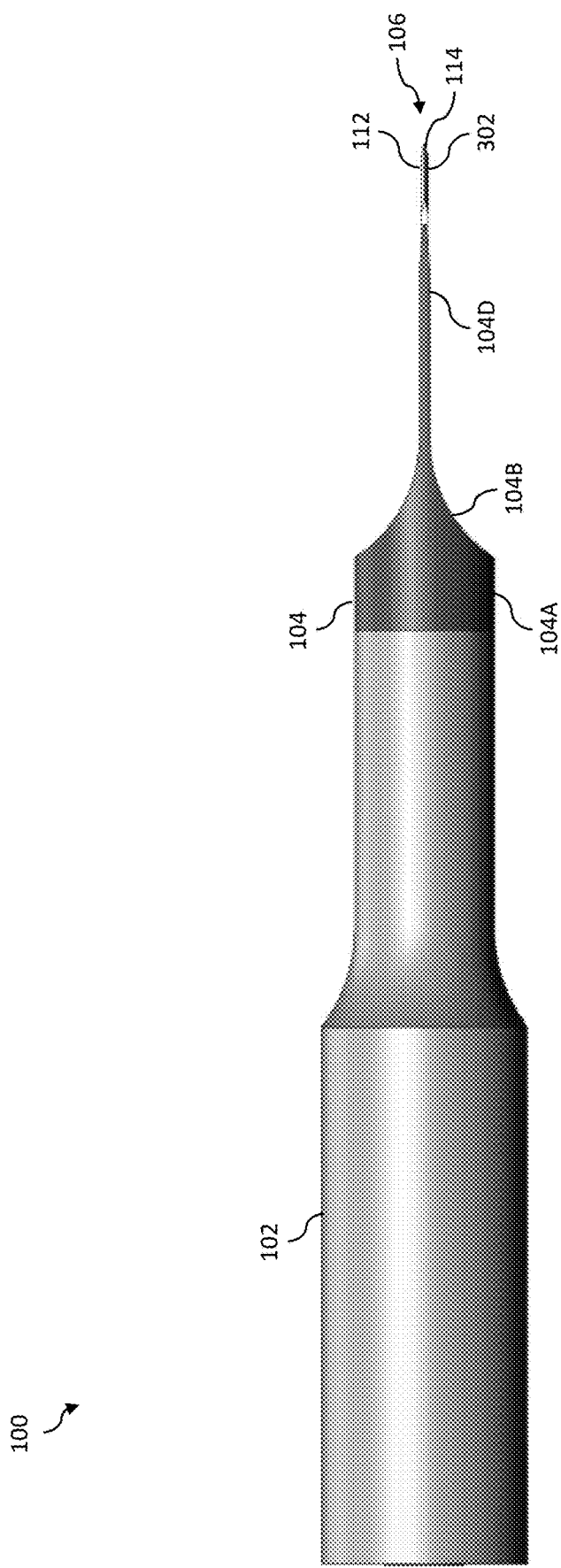
Figure 3:
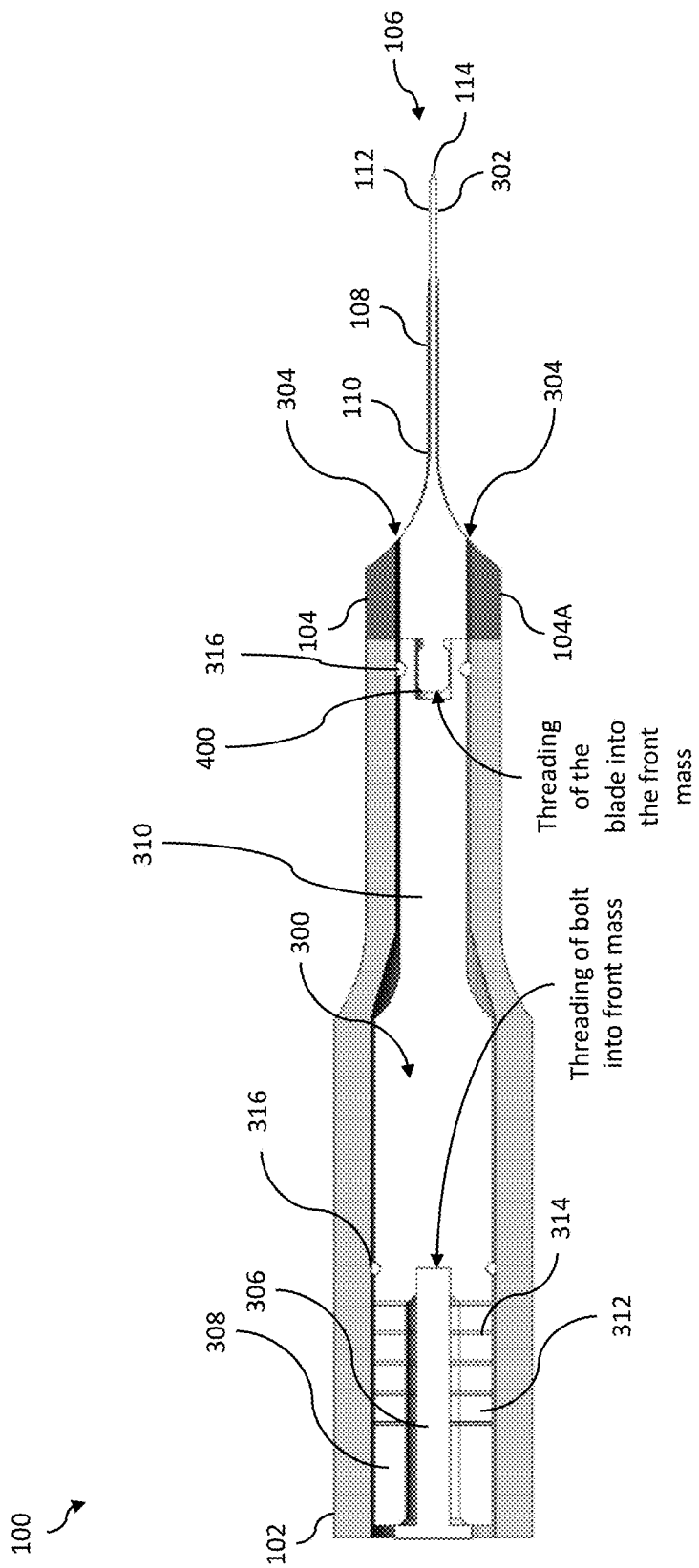
Figure 4:
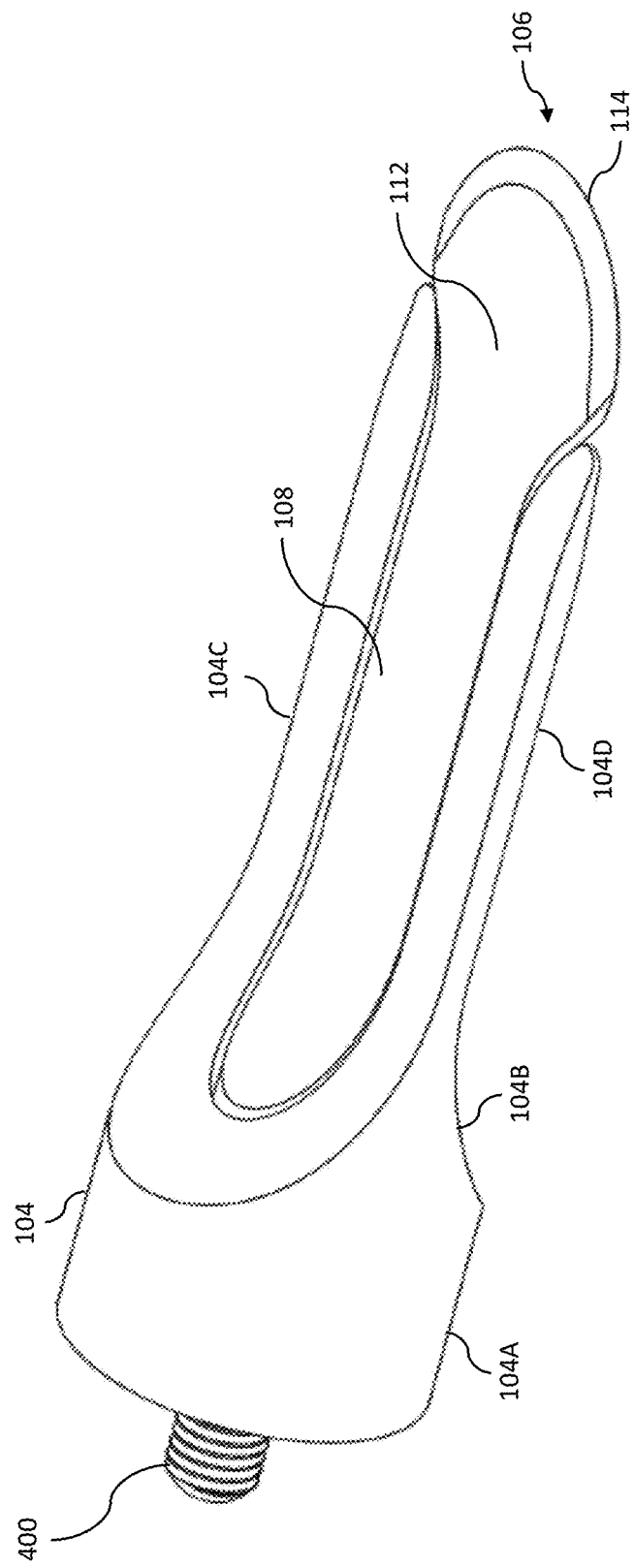
Figure 5:
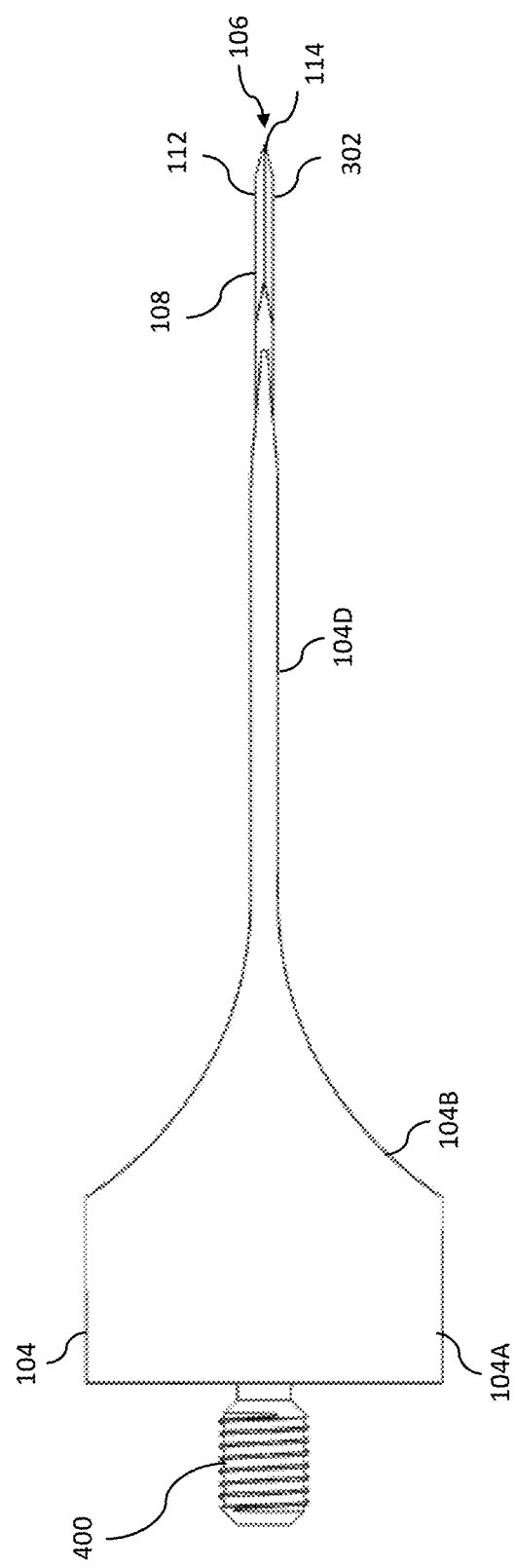
Figure 6:
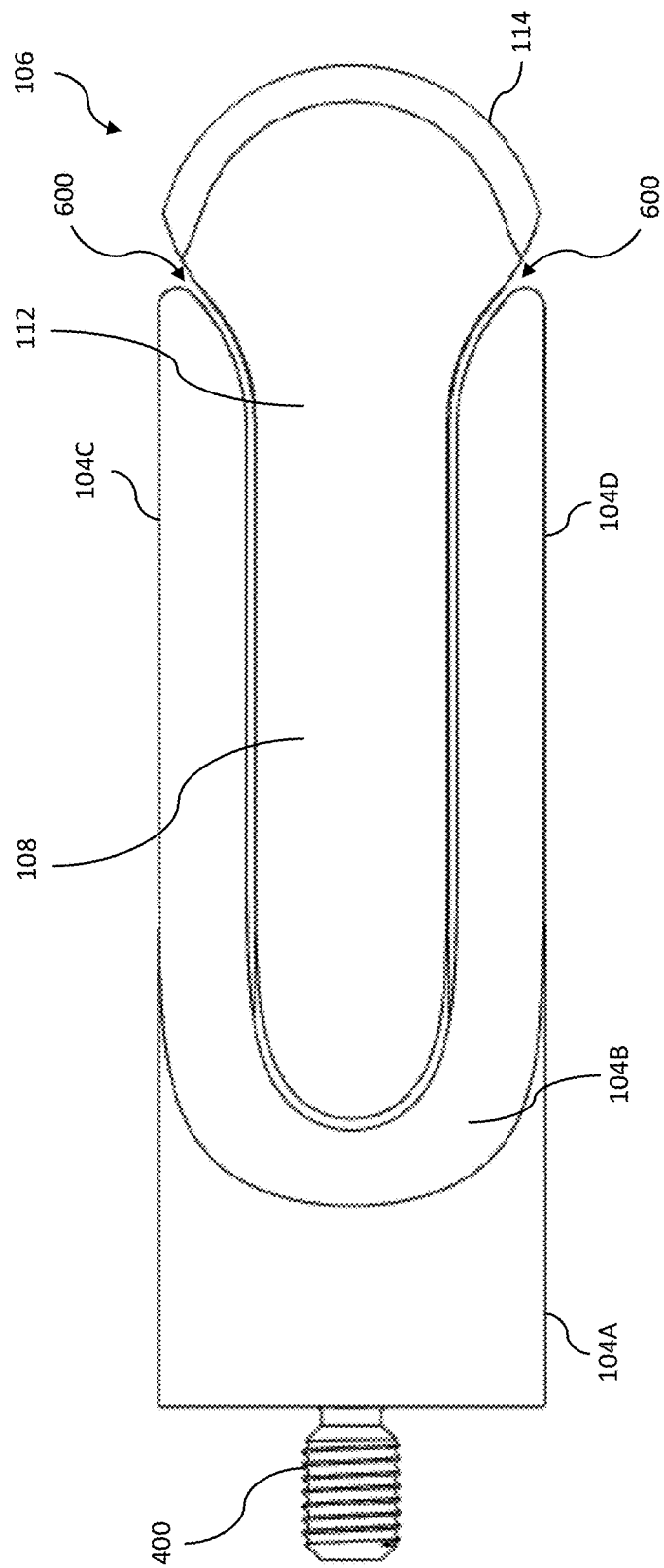
Figure 7:
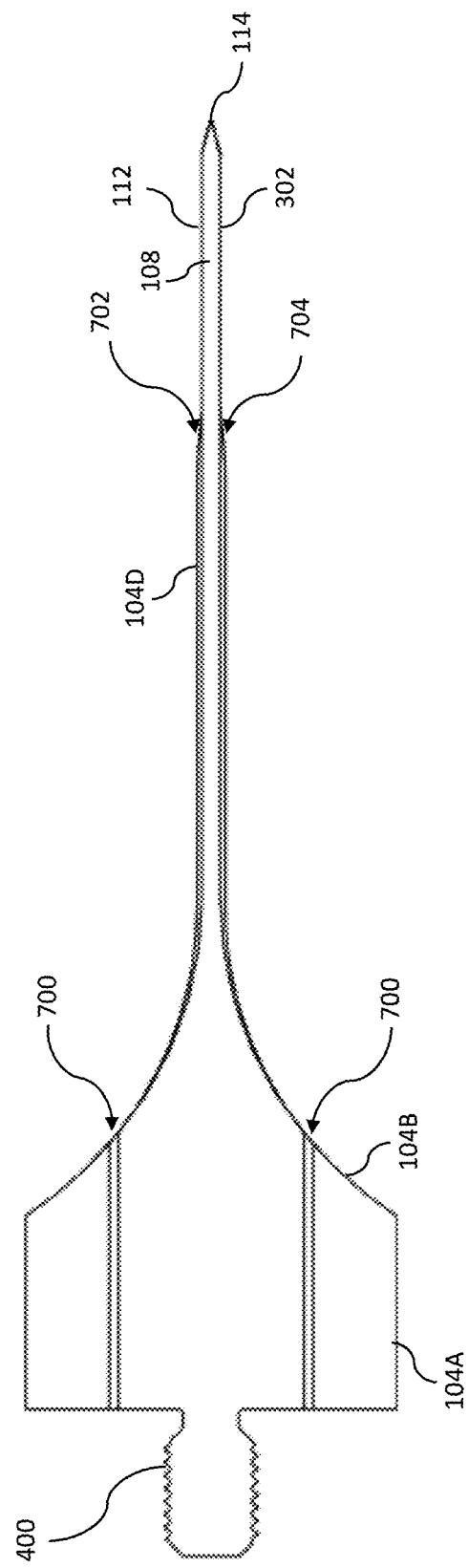
Figure 8:
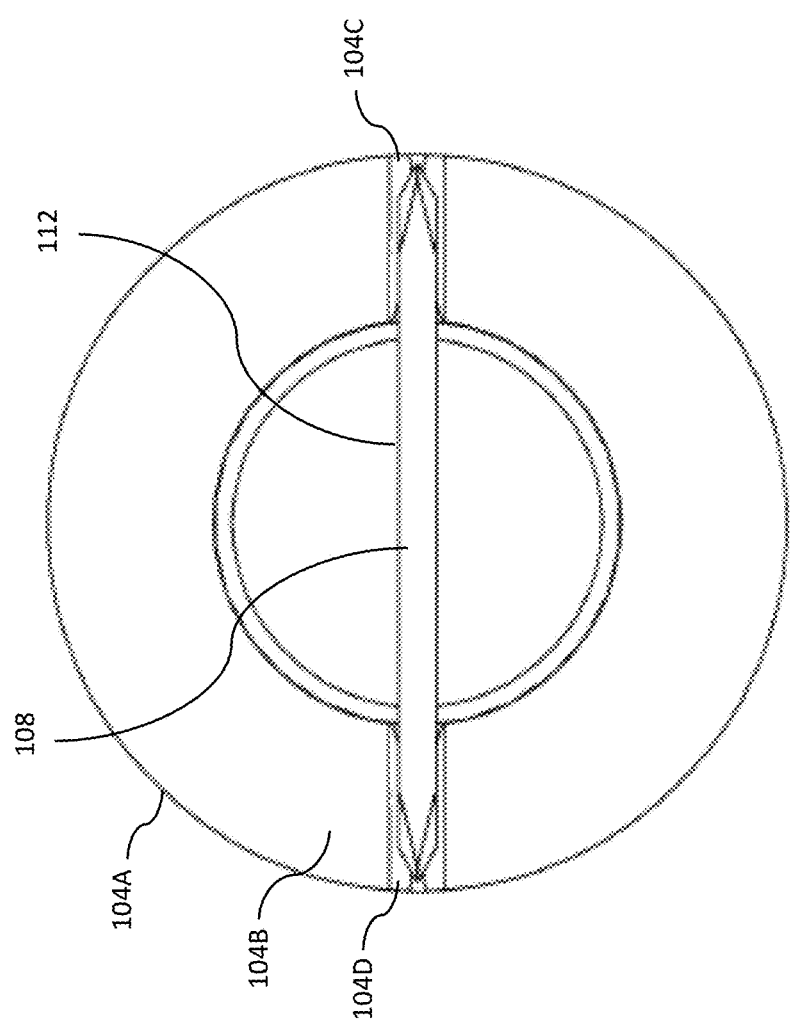
Figure 9:
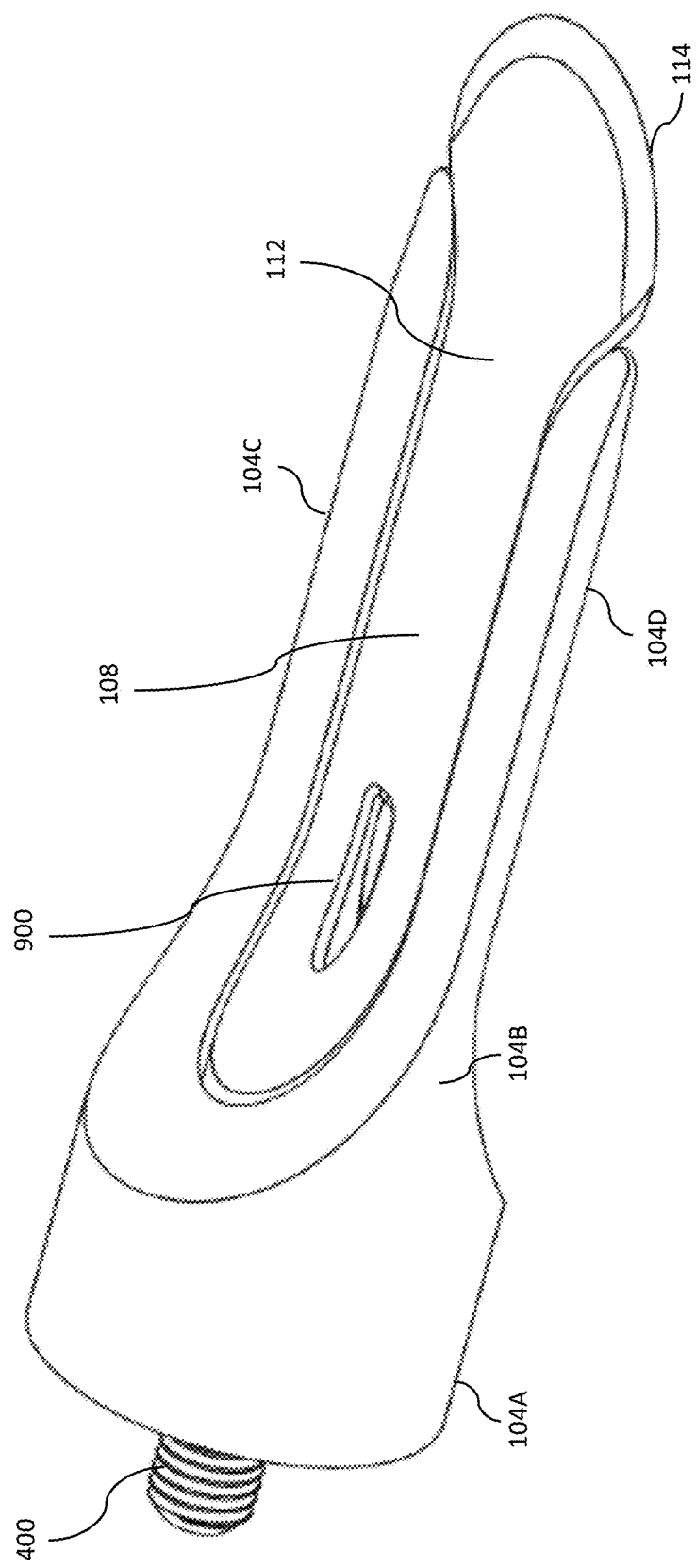
Figure 10:
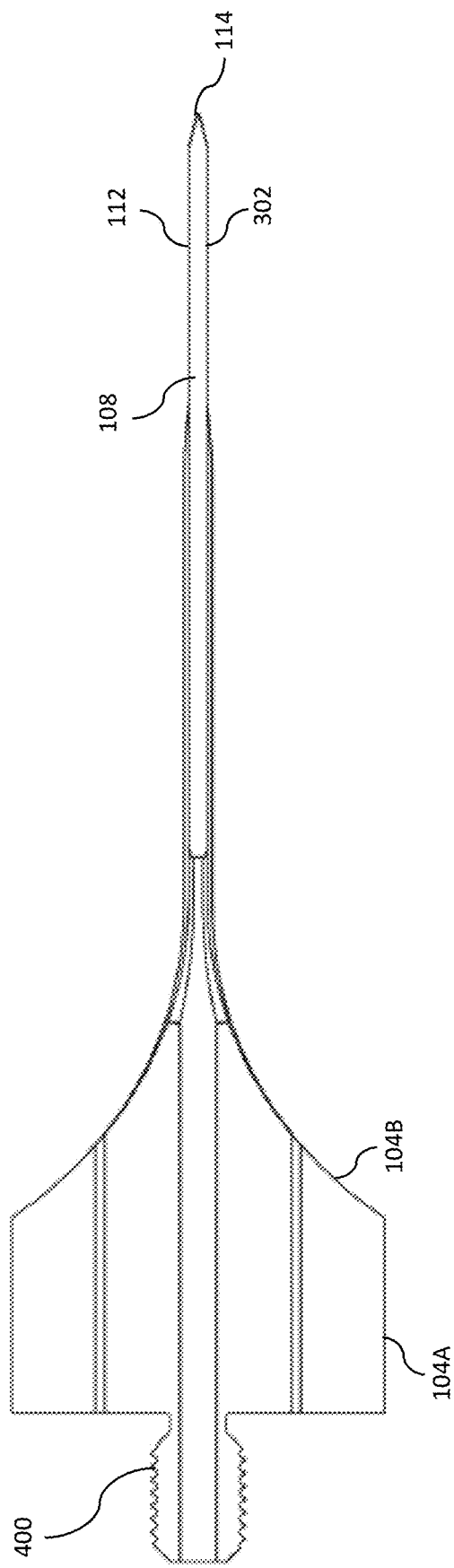
Figure 15:
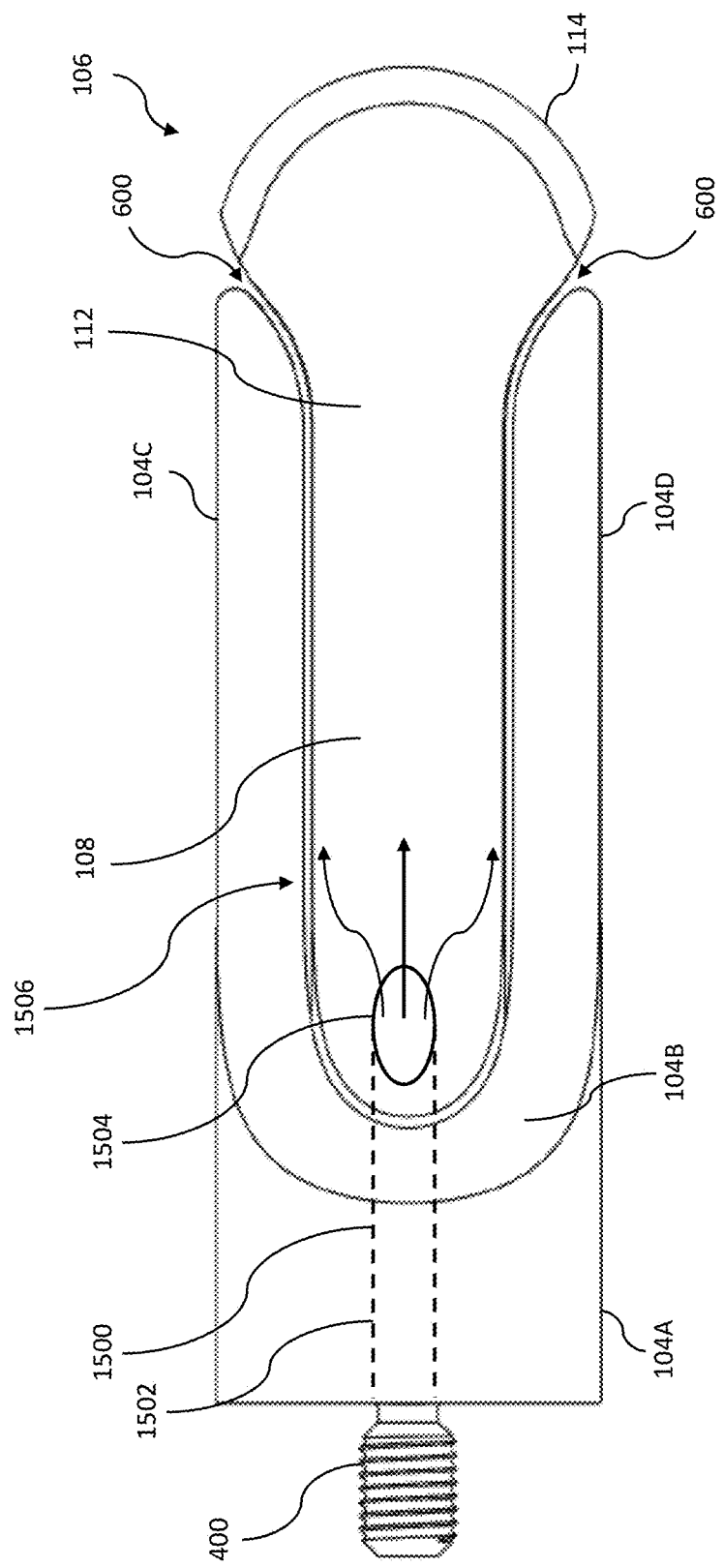
Figure 16A:
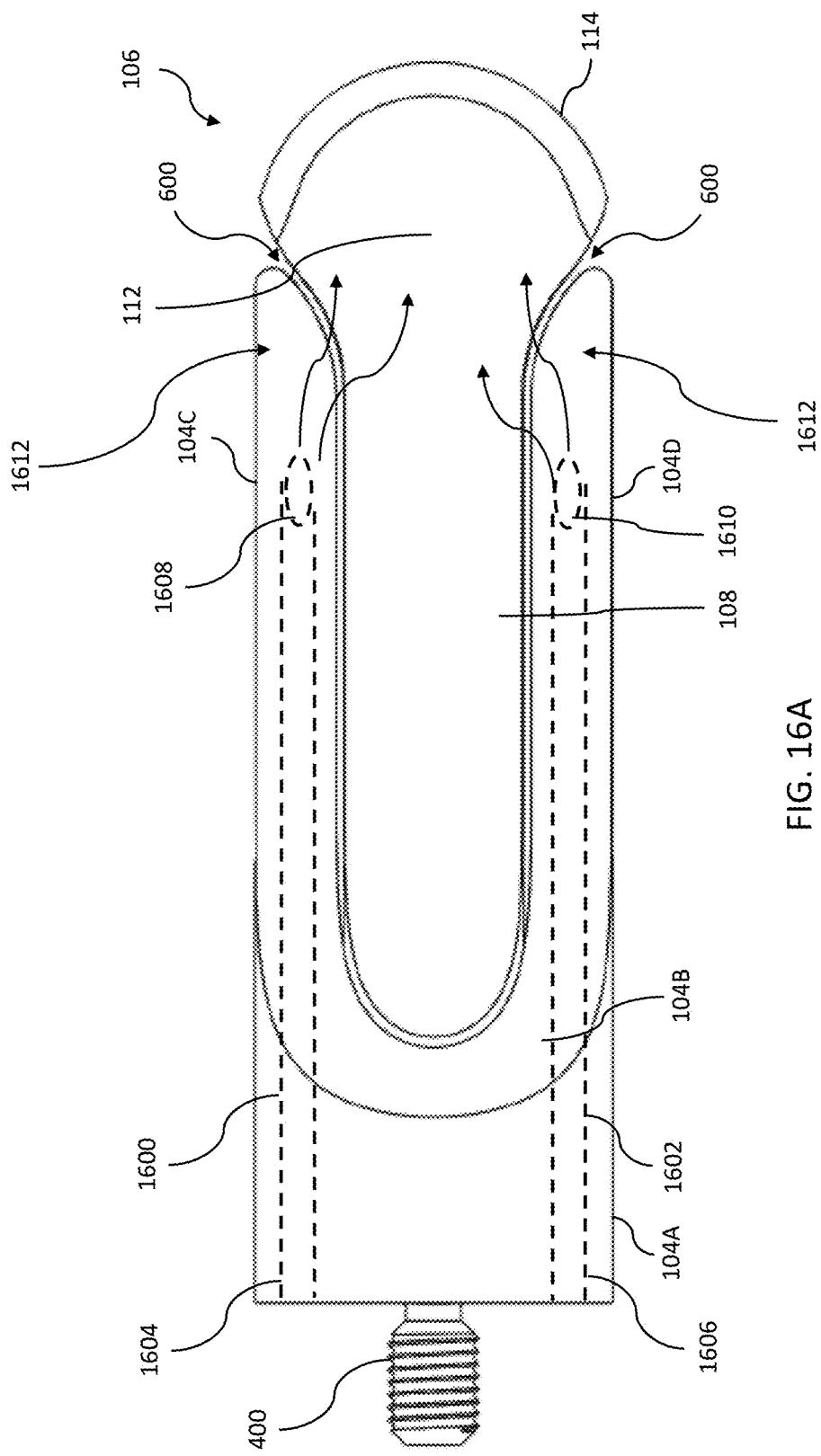
Figure 16B:
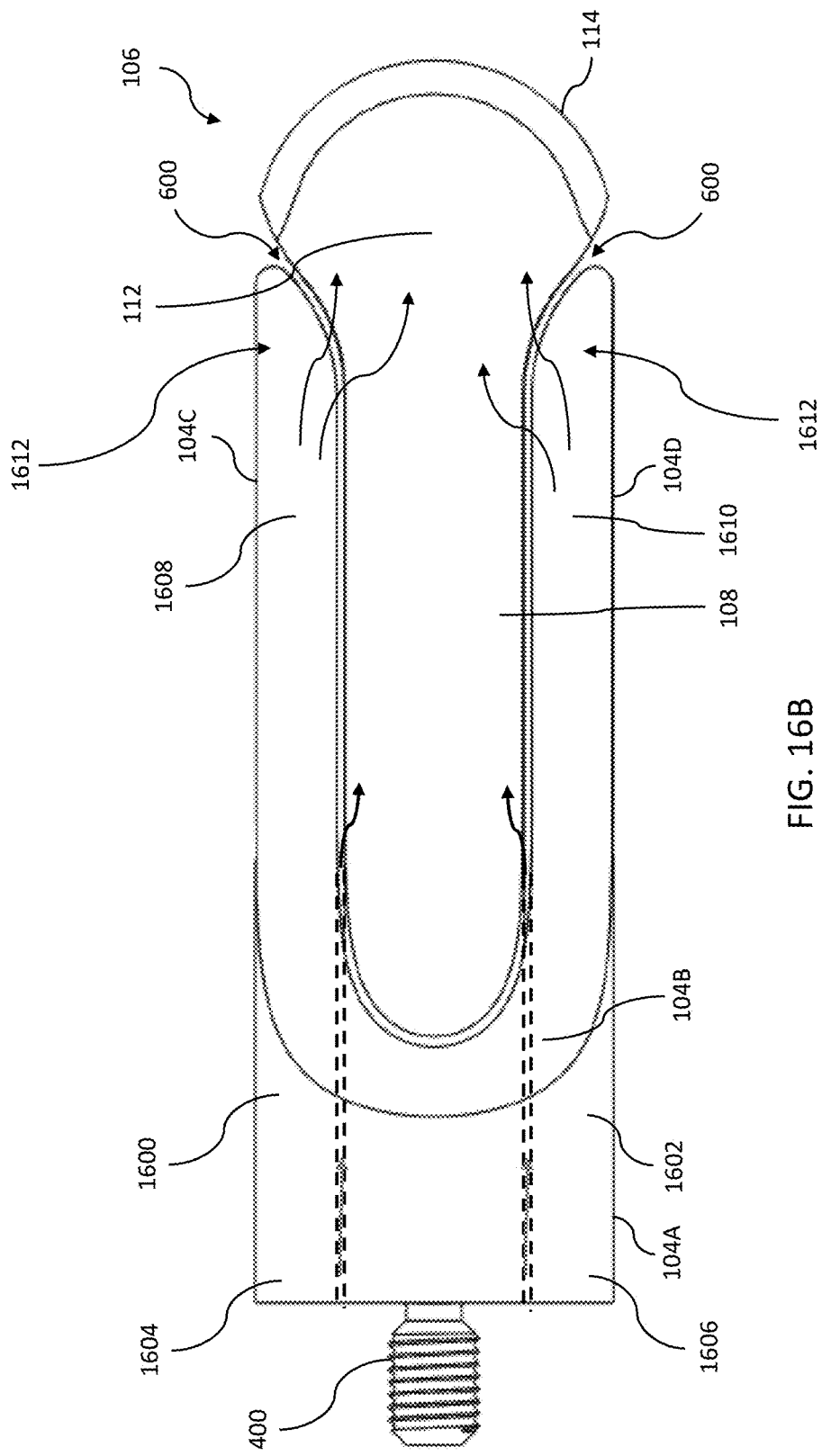
Figure 17:
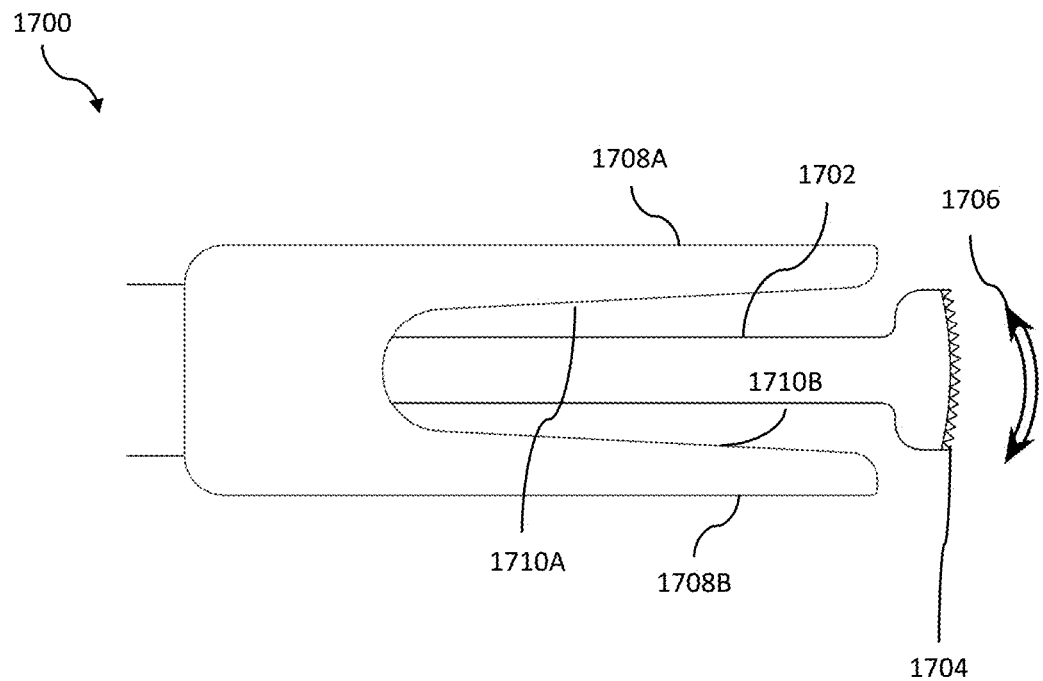
Figure 18:
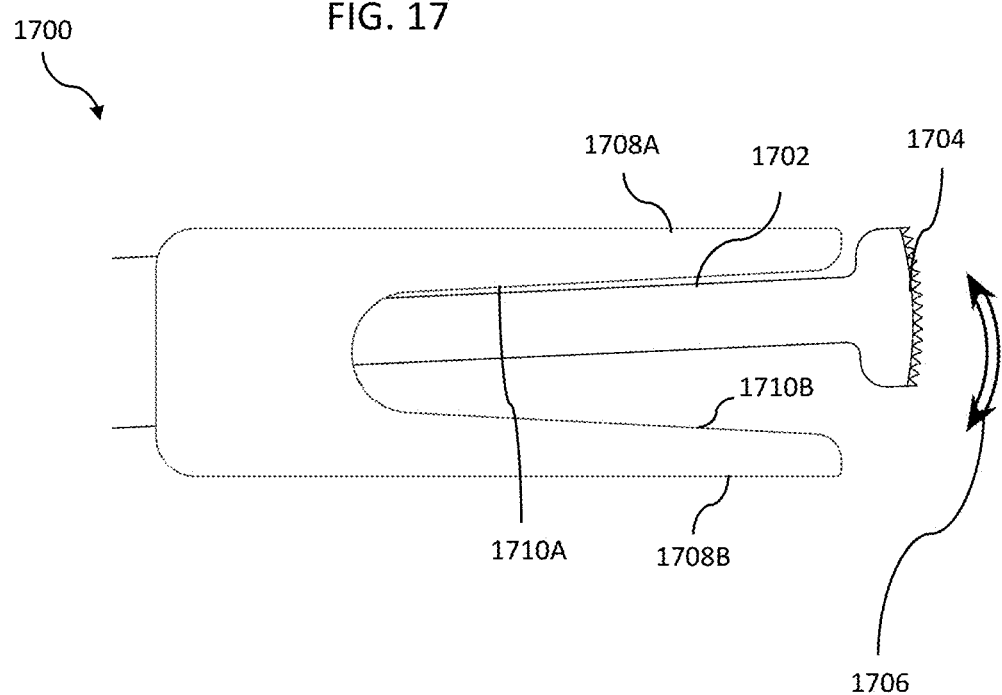
Figure 19:
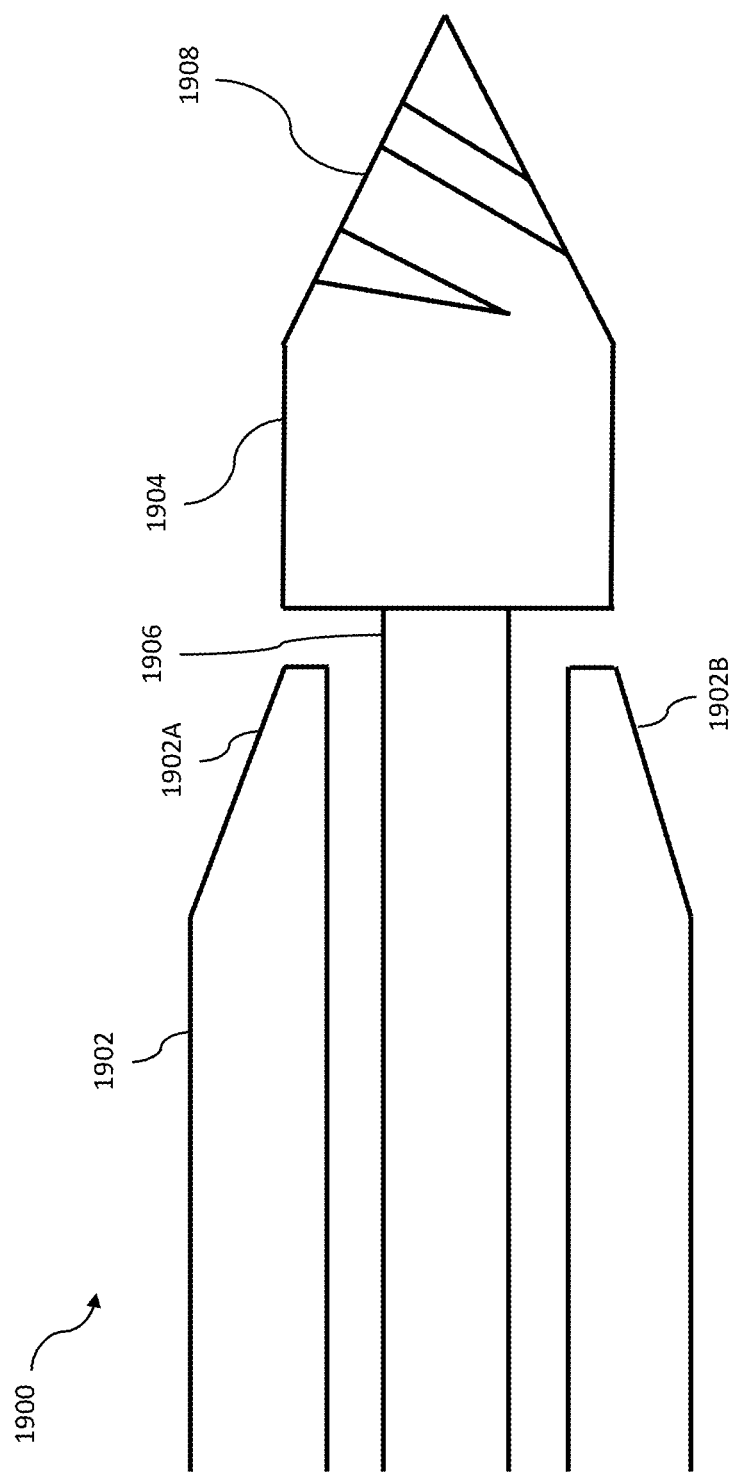
Figure 20A:
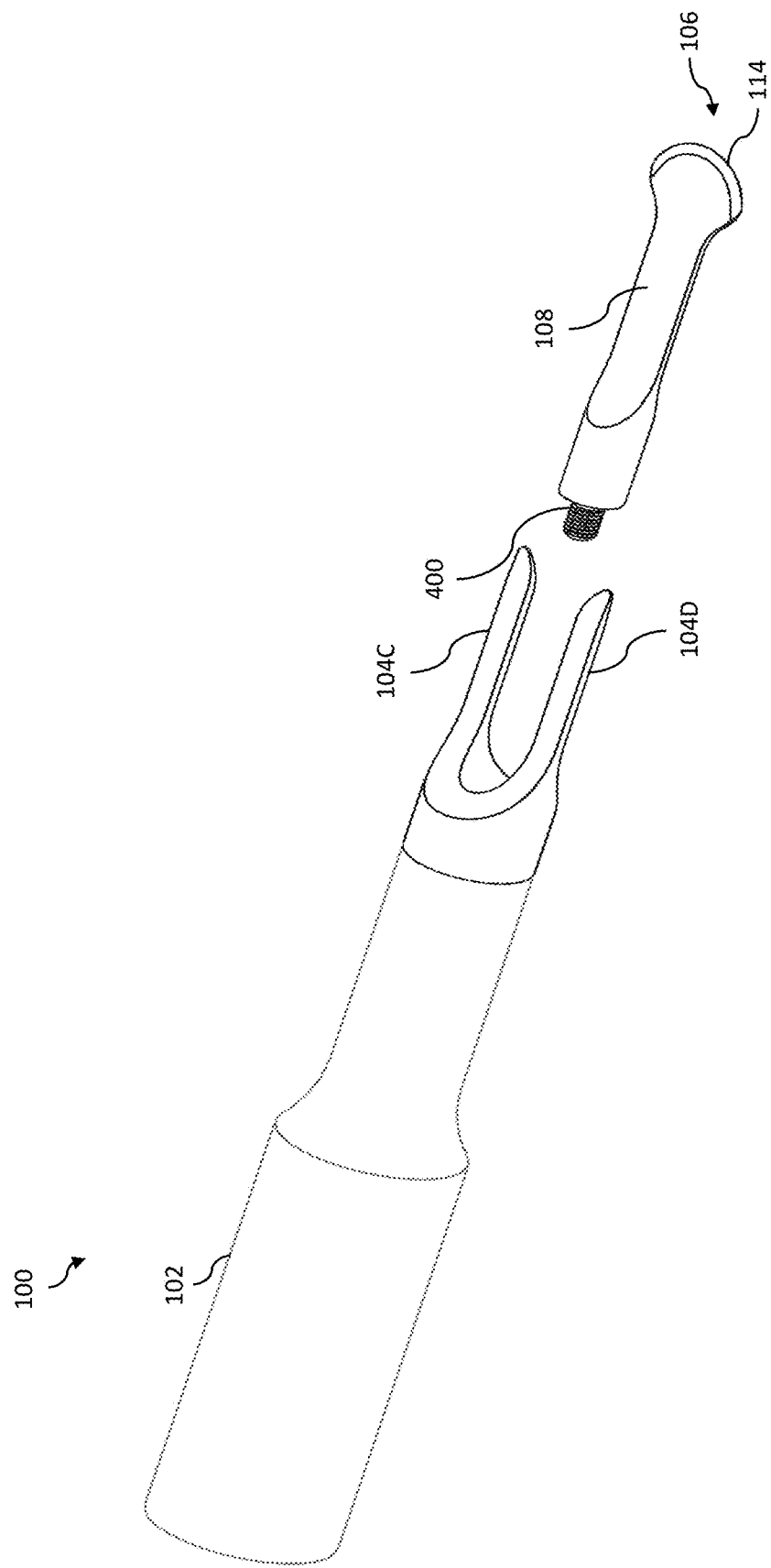
Figure 20B:
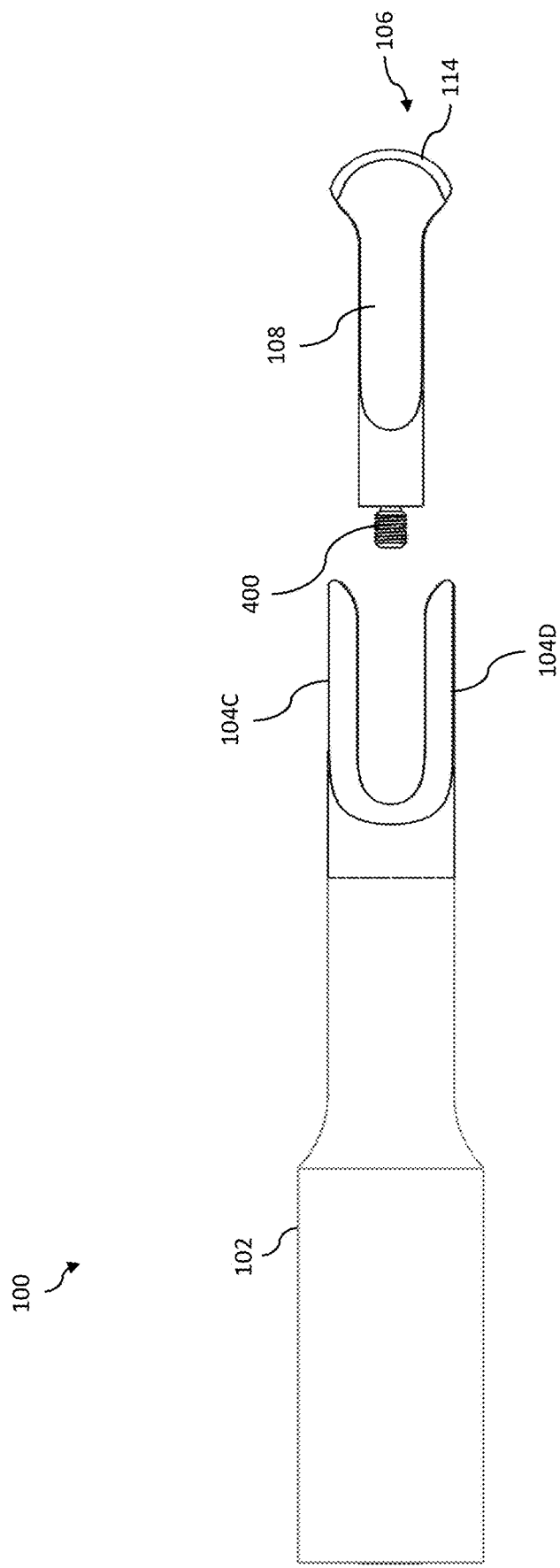
Figure 20C:
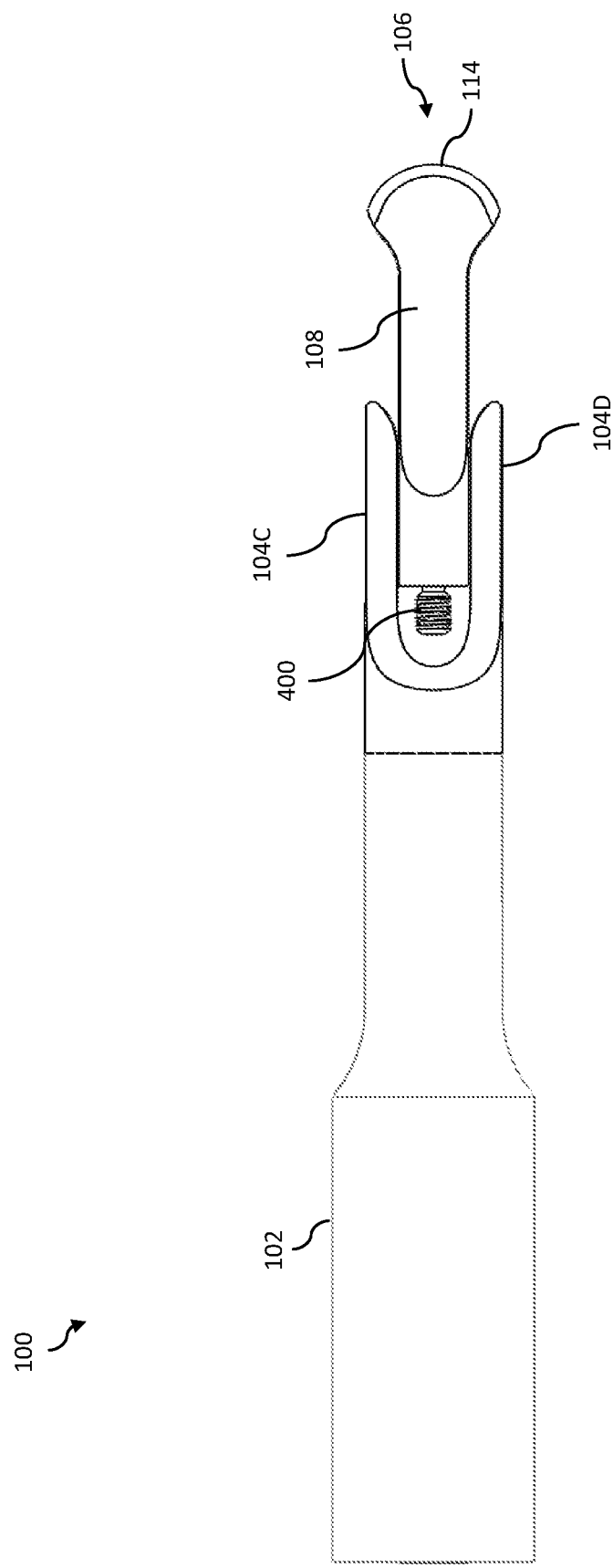
Figure 20D:
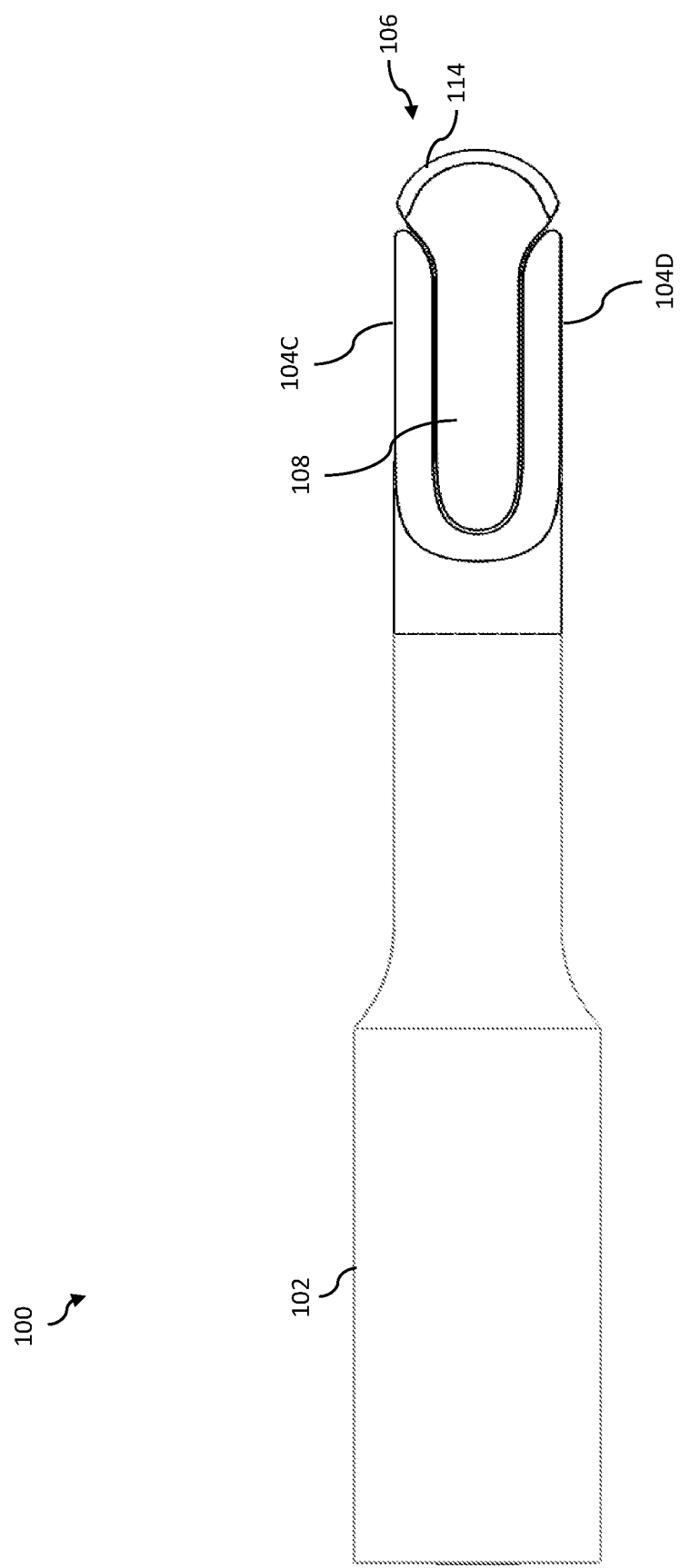
Figure 21A:
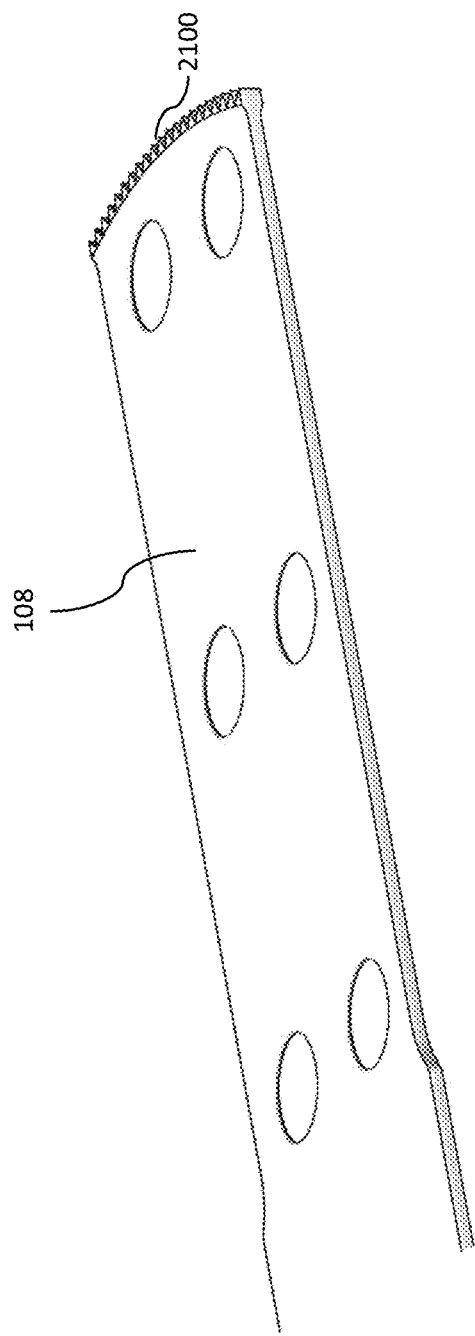
Figure 21B:
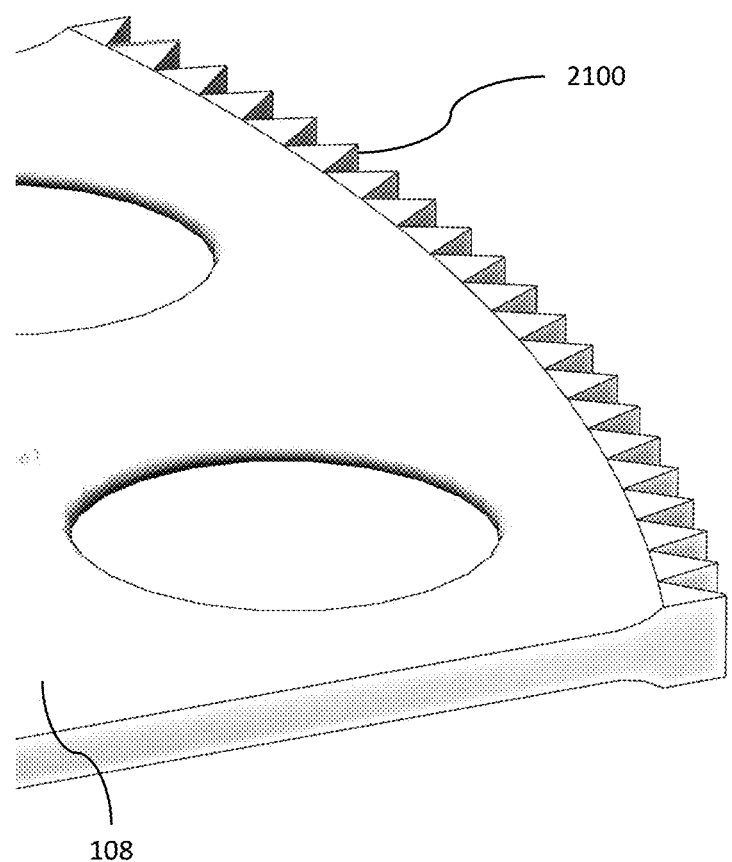
Figure 21C:
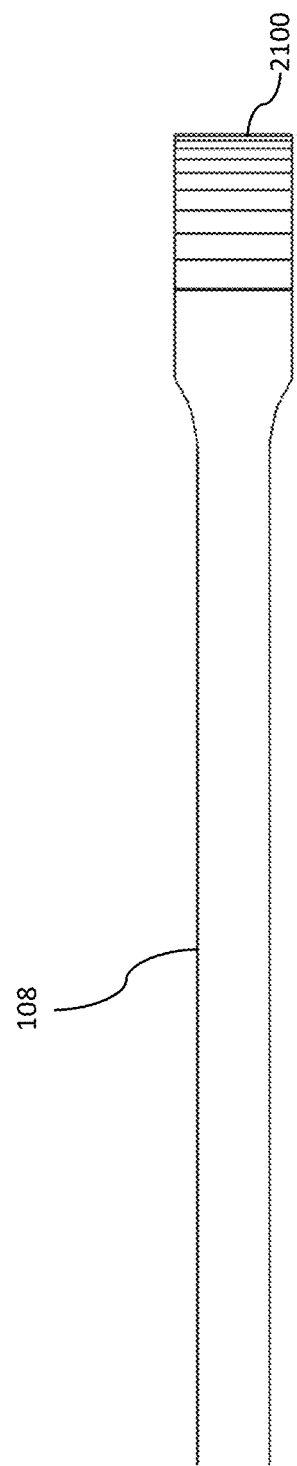
Figure 22A:
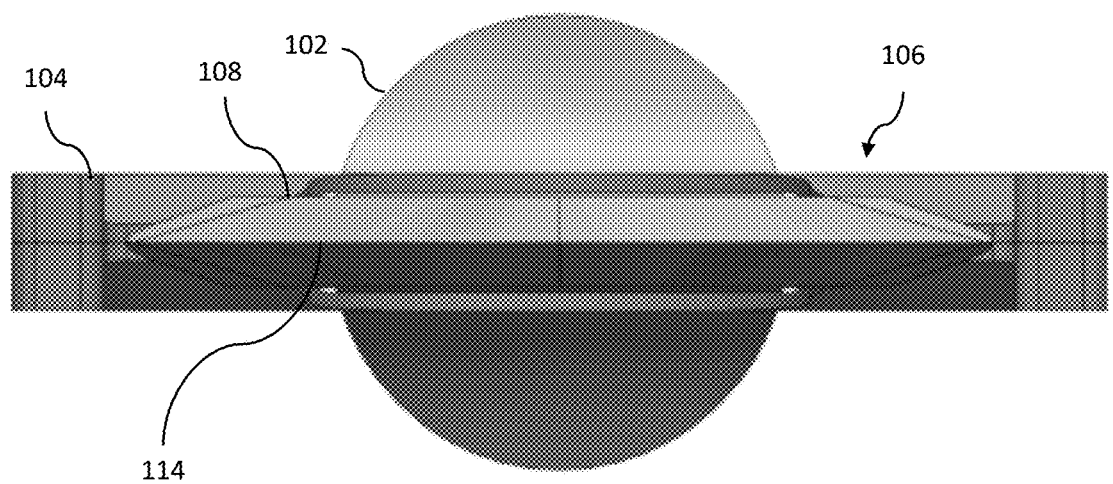
Figure 22B:
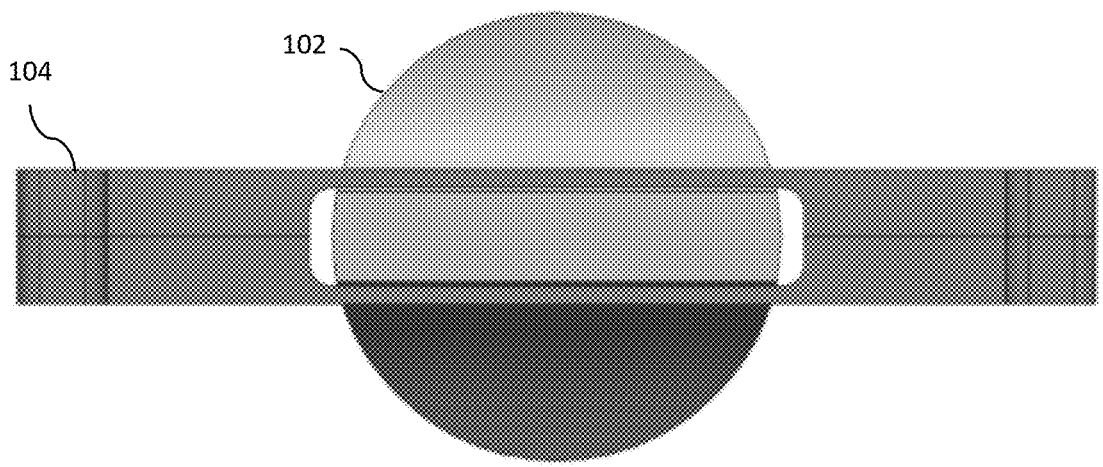
Figure 22C:
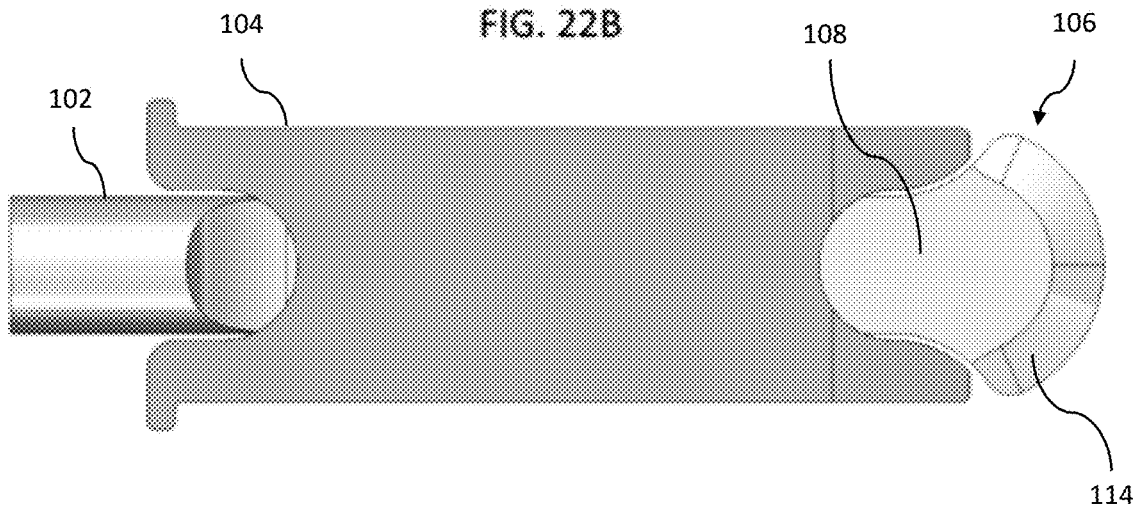
Figure 22D:
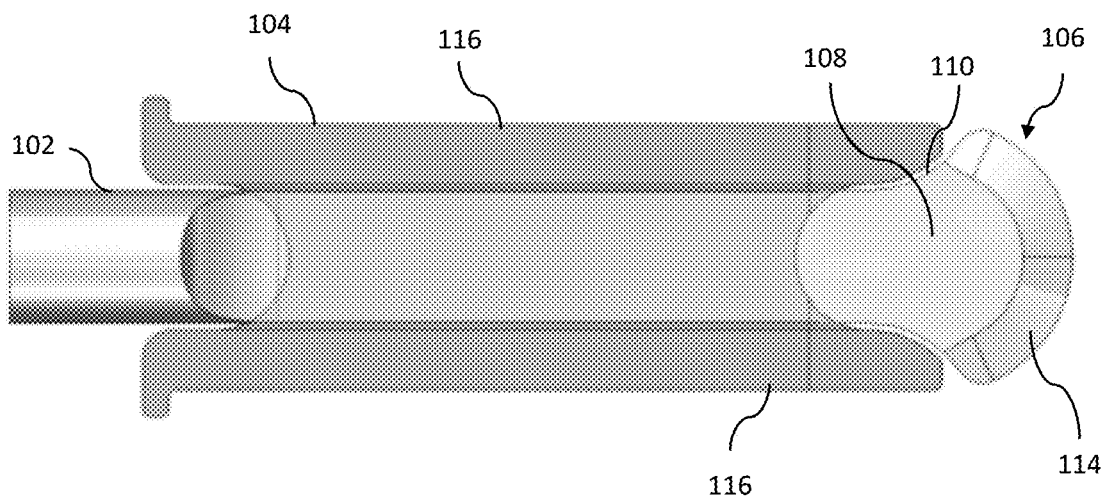
Figure 22E:
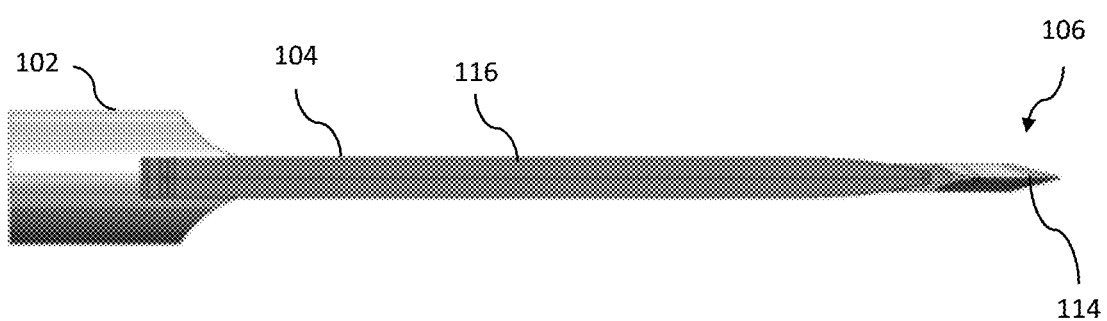
Figure 22F:
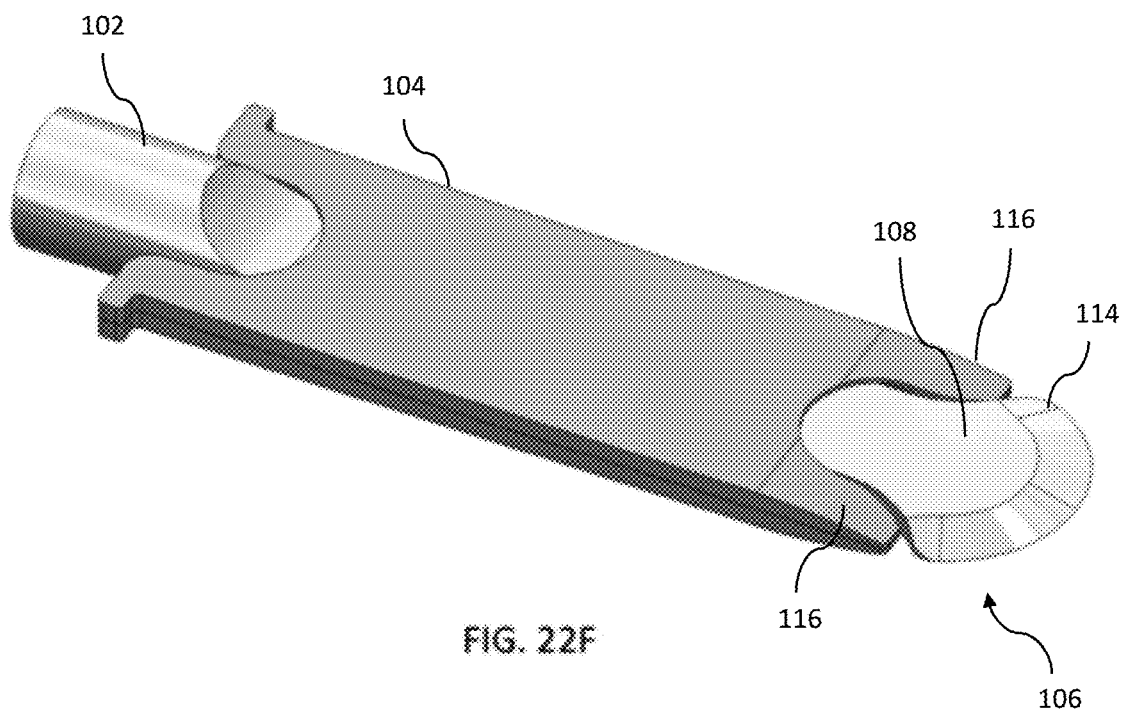
Figure 22G:
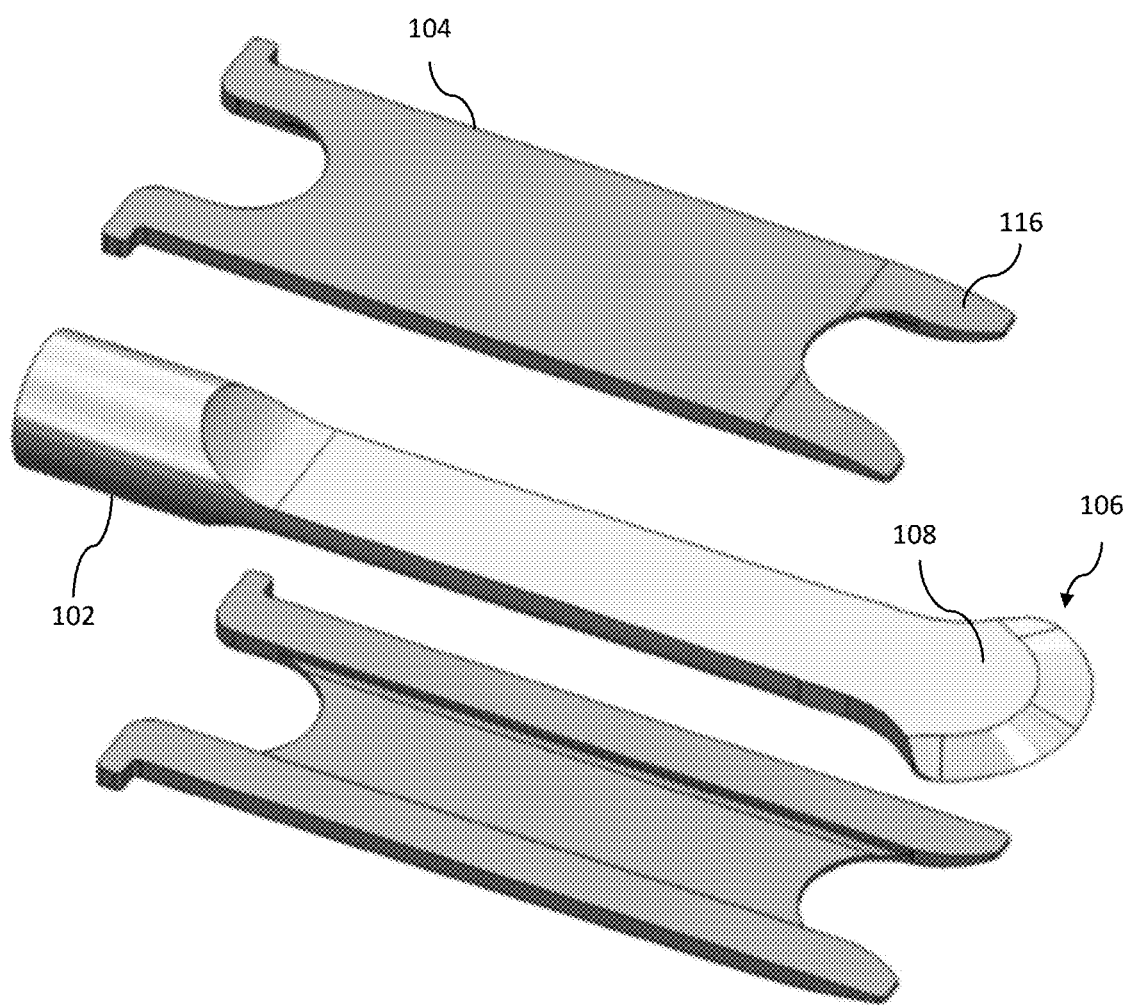
Figure 22G:
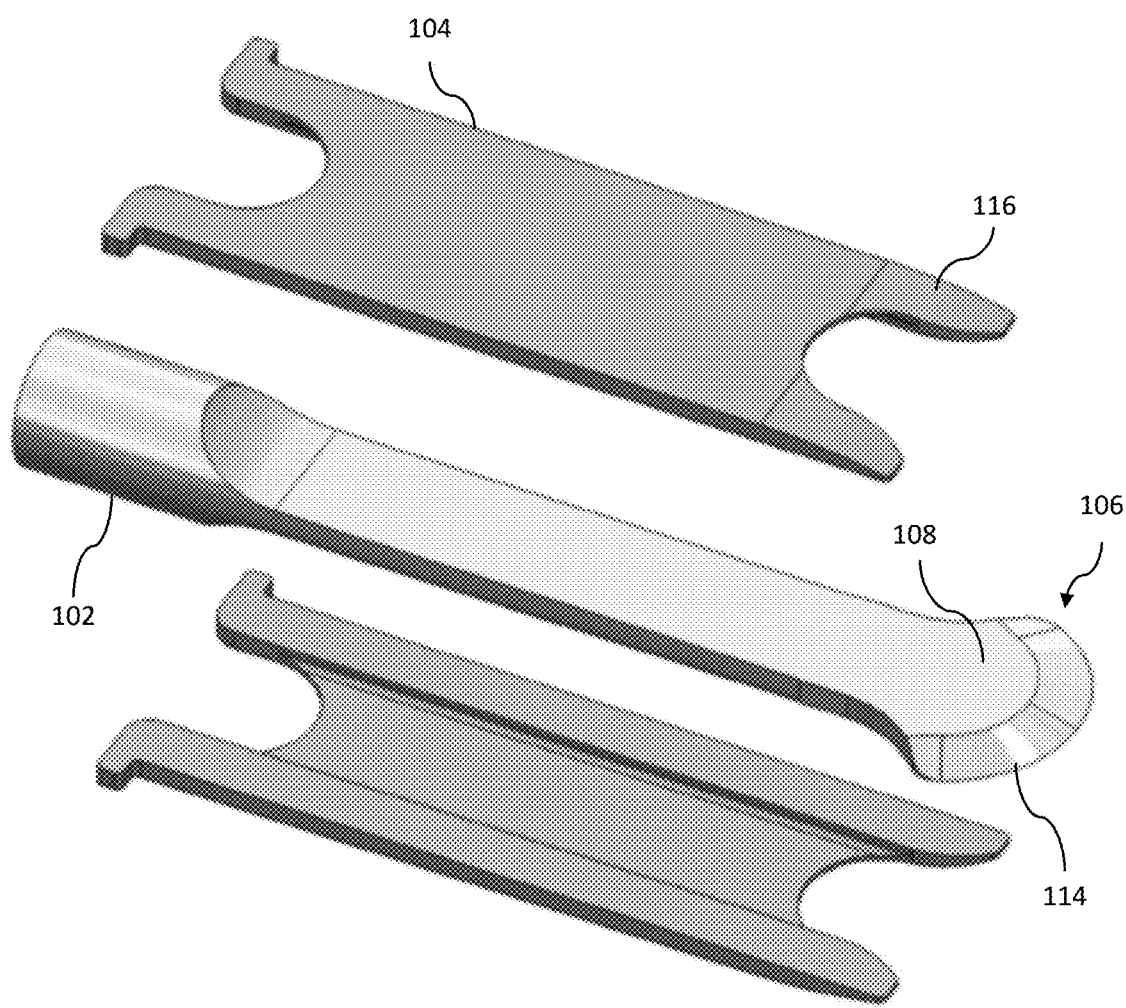

Having thus described the presently disclosed subject matter in general terms, reference will now be made to the accompanying Drawings, which are not necessarily drawn to scale, and wherein:

FIGS. 1, 2, and 3 illustrate a perspective view, a side view, and a cross-sectional side view, respectively, of a cutting device in accordance with embodiments of the present disclosure;

FIGS. 4, 5, 6, and 7 illustrate a perspective view, a side view, a top view, and a cross-sectional side view, respectively, of the static casing and the cutting end shown in FIGS. 1-3;

FIG. 8 illustrates a front cross-sectional view of the static casing and the cutting end shown in FIGS. 4-7 and transversed along the cutting end;

FIGS. 9 and 10 illustrate a perspective view and a cross-sectional side view of a static casing and a cutting end having a channel for transporting cooling fluid in accordance with embodiments of the present disclosure;

FIGS. 11-14 illustrate a time sequence of a side view of the device being operated to cut into bone in accordance with embodiments of the present disclosure;

FIG. 15 illustrates a top view of the static casing and the cutting end having an internal fluid channel in accordance with embodiments of the present disclosure;

FIG. 16A illustrates a top view of the static casing and the cutting end having multiple internal fluid channels within the side portions of the static casing in accordance with embodiments of the present disclosure;

FIG. 16B illustrates a top view of another static casing and cutting end having multiple internal fluid channels within the side portions of the static casing in accordance with embodiments of the present disclosure;

FIGS. 17 and 18 illustrate top views of a cutting device in different positions in accordance with embodiments of the present disclosure;

FIG. 19 illustrates a top view of a drilling device in accordance with embodiments of the present disclosure;

FIGS. 20A-20D illustrate a top perspective view and top views depicting some assembly of a cutting device in accordance with embodiments of the present disclosure;

FIGS. 21A-21C illustrate a top perspective view, a close-up perspective view, and a side view of a cutting device having a cutting end with a raised blade edge in accordance with embodiments of the present disclosure; and FIGS. 22A-22G illustrate a front view, a front section view, a top view, a bottom view, a side view, a top perspective view, and an exploded view, respectively, of a cutting device in accordance with embodiments of the present disclosure.

SUMMARY

The presently disclosed subject matter medical devices and related methods for transforming bone, other tissue, or material. According to an aspect, a cutting device includes a static casing that defines a sheathing slot and an opening. The sheathing slot extends to the opening and has a first height at an end of the opening. Further, the cutting device includes an ultrasonic horn including a first end and a second end. The first end is configured to operatively connect to a source of movement. Further, the second end includes a cutting component having a second height. The first height is greater than the second height.

According to another aspect, a transforming device includes a static casing that defines a sheathing slot and an opening. The sheathing slot extends to the opening and has a first height at an end of the opening. Further, the transforming device includes a drilling device including a first end and a second end. The first end is configured to operatively connect to a source of rotational movement. Further, the second end includes a drill bit. Also, the drilling device is separated from the static casing by a plurality of gaps.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

FIGS. 1, 2, and 3 illustrate a perspective view, a side view, and a cross-sectional side view, respectively, of a cutting device 100 in accordance with embodiments of the present disclosure. The device 100 includes a housing 102 and a static casing 104. Although these components are not shown in FIGS. 1, 2, and 3, the housing 102 may contain in an interior space 300 (shown in FIG. 3) therein components such as a piezoelectric transducer a transducer backing material, and other components for generating and propagating ultrasonic vibrations to a cutting end, generally designated 106. The piezoelectric transducer, which may be suitably powered to produce ultrasonic vibrations, can be operatively attached to an end of an ultrasonic horn 108 that is closest to the housing 102. Ultrasonic vibrations produced by the piezoelectric transducer can propagate along a main body of the ultrasonic horn 108 towards an end of the ultrasonic horn 108 that opposes the end of the ultrasonic horn 108 that is attached to the piezoelectric transducer. The static casing 104 sheaths the ultrasonic horn 108 and can be positioned within a sheathing slot 110 located along the central longitudinal axis of the static casing 104. The ultrasonic horn 108 and the sheathing slot 110 can be spaced from each other by an air gap or otherwise separated from each other by a suitable material, such as a lubrication film. The air gap can reduce transfer of vibrational energy from the ultrasonic horn 108 and, thus, heat to the static casing 104.

An exterior of the static casing 104 may be defined by a cylindrically-shaped portion 104A near the housing and an end 104B having two side portions 104C, 104D that taper in the direction towards the cutting end 106.

The cutting end 106 can be a blade tip configured to cut, ablate, abrade or otherwise transform, for example, bone or other tissue. The cutting end 106 includes a top surface 112 and an opposing bottom surface 302 (shown in FIGS. 2 and 3). The cutting end 106 defines at least one blade edge 114. In this example, the blade edge 114 is a continuous, planar arc, and sharpened along its entirety. In the alternative, the blade edge 114 may have serrations or any other type of edge suitable for cutting, ablating, abrading, or otherwise transforming bone or other tissue.

As shown, the side portions 104C and 104D of static casing 104 each define longitudinal edges 116. The edges 116 may be filleted or substantially rounded. The static casing 104 may be made of a material suitable for biomedical applications, such as ceramic, titanium, stainless steel, PEEK, PE, PTFE, or the like. The outer surface of the static casing 104 may be coated with a lubricant, such as a solid film or a fluid film. The ultrasonic horn 108 may be made of a material suitable for biomedical applications, such as titanium, stainless steel, PEEK, PE, PTFE, or the like. In embodiments, a lubrication film may cover the ultrasonic horn 108 and may be made of a solid film lubricant, a hydrodynamic lubricant, or other suitable lubricant. Further, for example, the sheathing slot 110 may be coated with a lubrication film, such lubrication film being a solid film lubricant suitable for the application. The sheathing slot 110 and the ultrasonic horn 108 may be coated with the lubrication film.

The aforementioned piezoelectric transducer can produce ultrasonic vibrations that are transferred to the ultrasonic horn 108, which concentrates or amplifies these vibrations at the cutting end 106. Movement of the cutting end 106 can generate heat, which can be detrimental to biological tissues that come in contact with the cutting end 106. In accordance with embodiments, one or more channels for transporting cooling fluid from a source to the cutting end 106 or near the cutting end 106 may be integrated into the device 100. Particularly, one or more internal channels may be defined within the ultrasonic horn 108, portion 104C, and/or portion 104D for transporting fluid from a source to location(s) near the cutting end 106. For example, the channel(s) may exit the ultrasonic horn 108, portion 104C, and/or portion 104D for cooling the cutting end 106 and/or biological tissue (e.g., bone). The fluid carried by the channel(s) may be a coolant such as saline. This fluid may inhibit the generation of heat, thereby reducing the likelihood of damage to the tissue. In addition, fluid flowing within the ultrasonic horn 108, portion 104C, and/or portion 104D can insulate for preventing transfer of heat.

Turning now specifically to FIG. 3, it is shown that the static casing 104 is directly attached to an end of the housing 102 such that there is no contact of the static casing 104 to either the cutting end 106 or the ultrasonic horn 108. For example, reference numerals 304 in FIG. 3 show air gaps between the static casing 104 and the ultrasonic horn 108. The air gaps 304 along the lengths of the static casing and the ultrasonic horn 108. These air gaps 304 can reduce the overall amount of heat generated by the device 100, because the surfaces of the ultrasonic horn 108 and the static casing 104 do not move against one another to generate thermal energy due to friction between the surfaces. Also, air gaps 600 and 700 can be seen in FIGS. 6 and 7, respectively.

An air gap 702 may be present between the top surface 112 of the cutting end 106 and the top of side portion 104D (and also side portion 104C, not shown in FIG. 7). Similarly, an air gap 704 may be present between the bottom surface 302 of the cutting end 106 and the top of side portion 104D (and also side portion 104C, not shown in FIG. 7). These air gaps can advantageously, for example, prevent or reduce transfer of vibrations from the cutting end 106 to the side portions 104C and 104D, and thereby the other portions of the static casing 104. The air gaps 702 and 704 can prevent transfer of thermal energy between the surfaces due to friction.

In the example of FIG. 3, Langevin transducer components are used to assist with assembly of the device. At the end furthest from the blade edge, a bolt 306 is provided that holds a back mass 308 and a front mass 310 of the transducer together and works to compress the piezoceramics 312 and corresponding electrodes 314. At the nodal planes of the device (in this example device there are two regions of zero ultrasonic vibrations that correspond to the nodal planes, demonstrating the device can operate as a full wavelength transducer in the $2^{nd}$ longitudinal mode of vibration) elastic O'rings 316 that support the housing from contacting the assembly in all other regions of vibration.

FIGS. 4, 5, 6, and 7 illustrate a perspective view, a side view, a top view, and a cross-sectional side view, respectively, of the static casing 104 and the cutting end 106 shown in FIGS. 1-3. A threaded member 400 provides a method of joining various functional cutting attachments to the transducer assembly. FIG. 8 illustrates a front cross-sectional view of the static casing 104 and the cutting end 106 shown in FIGS. 4-7 and transversed along the cutting end 106. Portions 104C and 104D taper to a height at their ends to a height above the height of the ultrasonic horn 108 for preventing contact of the blade on the bone or other tissue into which the blade is cutting or otherwise transforming.

FIG. 7 also demonstrates that since the tapered rails of the static casing 104 are higher than the working end of the blade, they provide a channel for wear debris generated at the blade edge to flow freely along the working surface of the blades between the rails (again lowering heat produced as a result of friction between the blade/bone debris/bone interfaces).

FIGS. 9 and 10 illustrate a perspective view and a cross-sectional side view of a static casing 104 and a cutting end 106 having a channel for transporting cooling fluid in accordance with embodiments of the present disclosure. Referring to FIGS. 9 and 10, the ultrasonic horn 108 defines an opening 900. In this embodiment, there is just a cannulation going through the threaded portion of the blade that becomes exposed to the top and bottom surfaces of the blade once it reaches the working surface after the blade has finished tapering to its final thickness. The opening for the fluid channel reaches a chamfered surface that splits the fluid in two directions, again above and below the working surface of the blade. In other embodiments, it is envisioned that a slot can extend the entire length or substantially the entire length of the device for providing an opening for the coolant fluid to flow.

Figure 11:
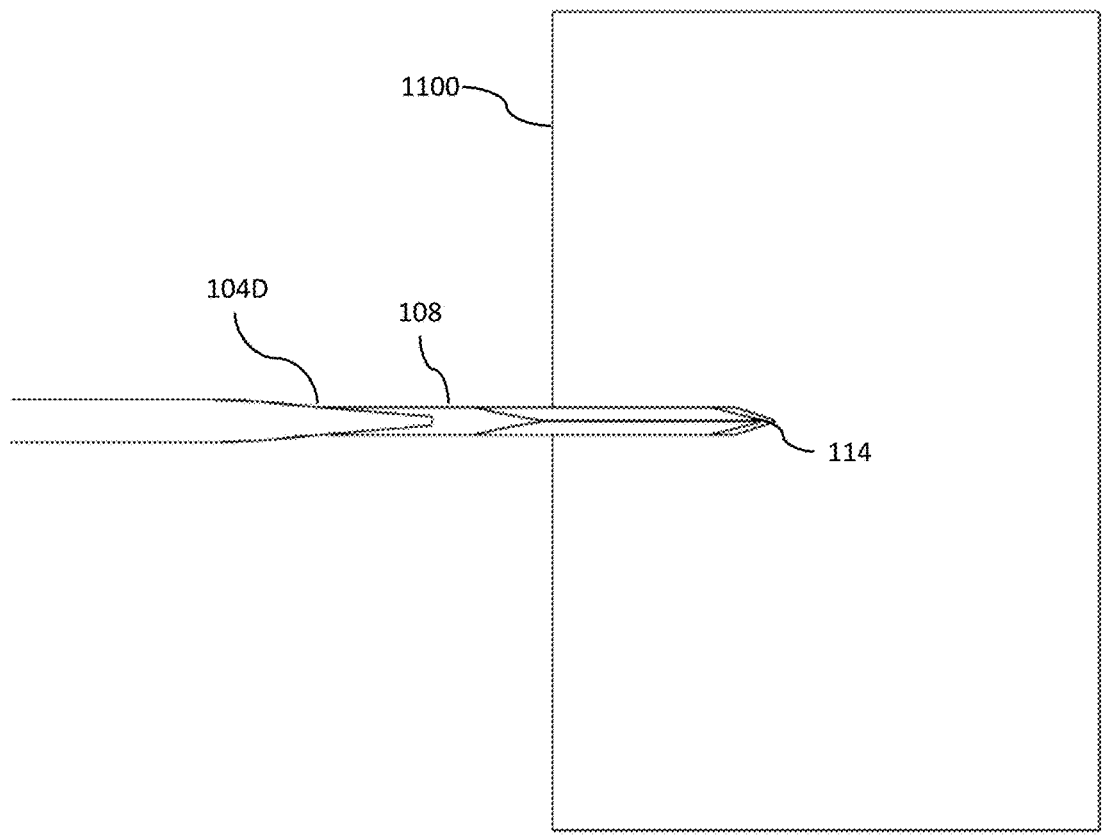
Figure 12:
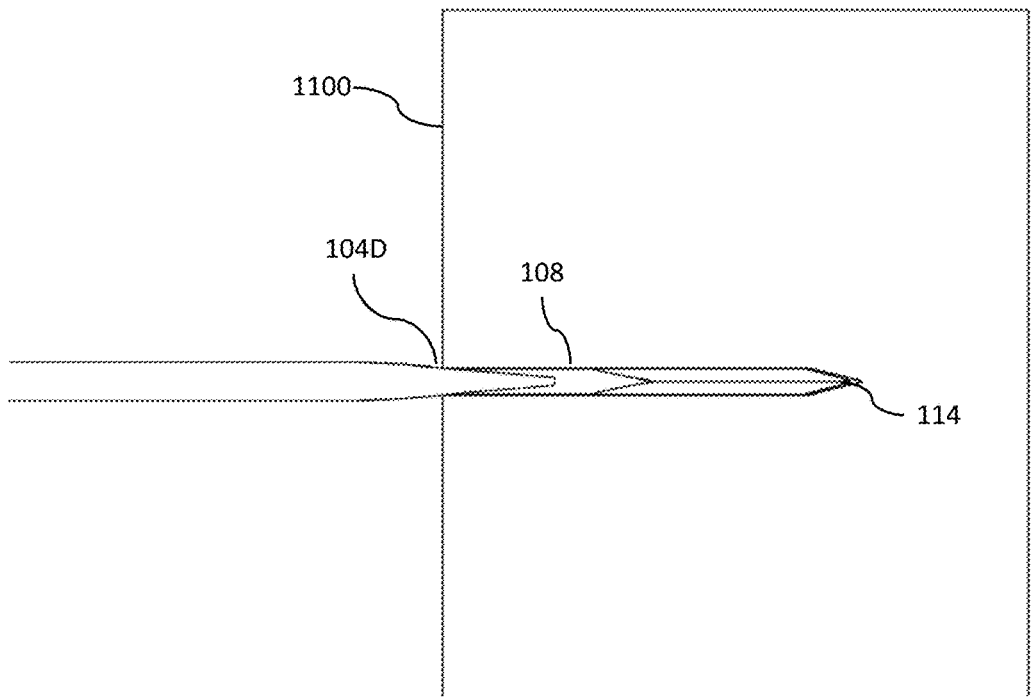

In accordance with embodiments, tapered portions of a static casing may be used for receiving a load force applied by bone or other tissue when the blade tip is cutting, ablating, abrading, or otherwise transforming the bone or other tissue. This may be when the blade tip is at a depth within the bone or other tissue such that the tapered portions reach the bone or other tissue. For example, FIGS. 11-14 illustrate a time sequence of a side view of the device being operated to cut into bone 1100 in accordance with embodiments of the present disclosure. It is noted that FIGS. 11-14 only shown an end of the device. Referring to FIG. 11, the figure shows a point in time at which the blade edge 114 has initially cut into the bone 1100 but not yet reached a depth such that the tapered portions 104D (or 104C, not shown) can touch the bone 1100. At the time of this figure, the load of the bone 1100 is entirely on the blade. Now referring to FIG. 12, it can be seen that the tapered portions 104D (and 104C, not shown) begin to contact the bone 110 in order to carry the load of the bone 1100 such that load on the blade is reduced and shifted away from the blade.

Figure 13:
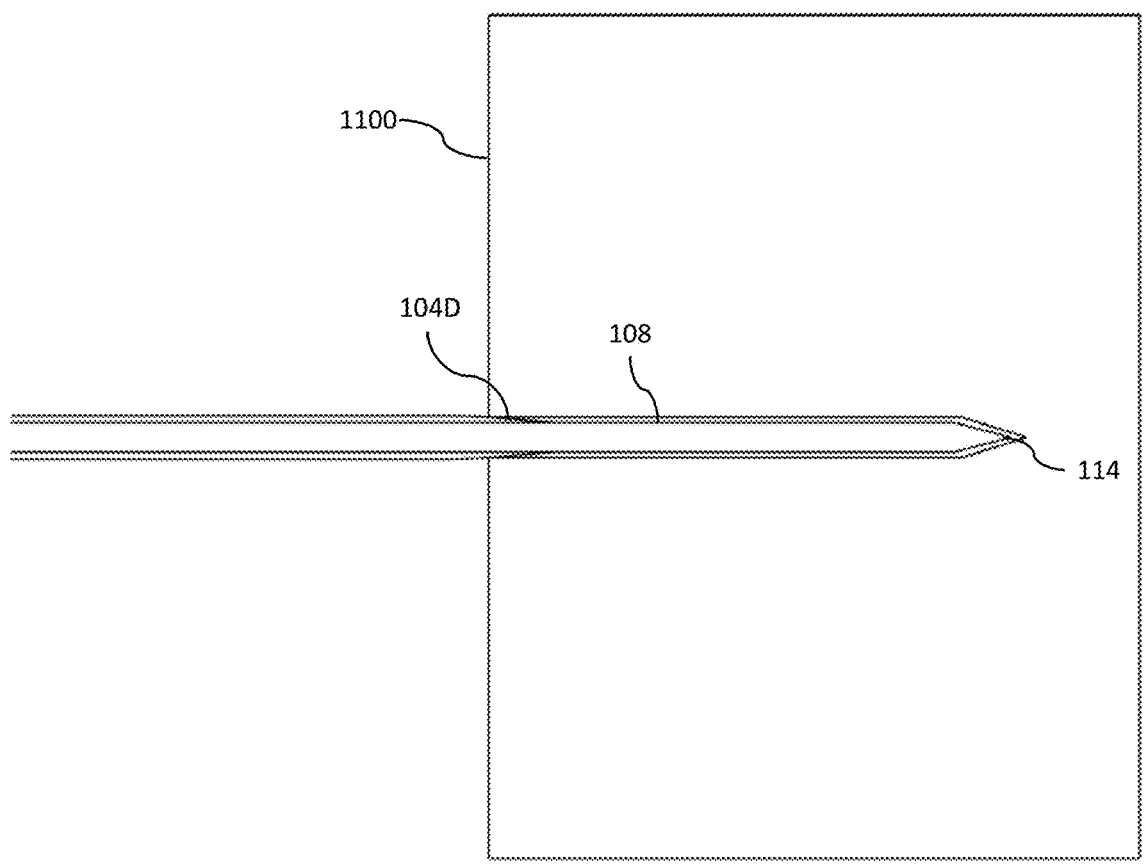
Figure 14:
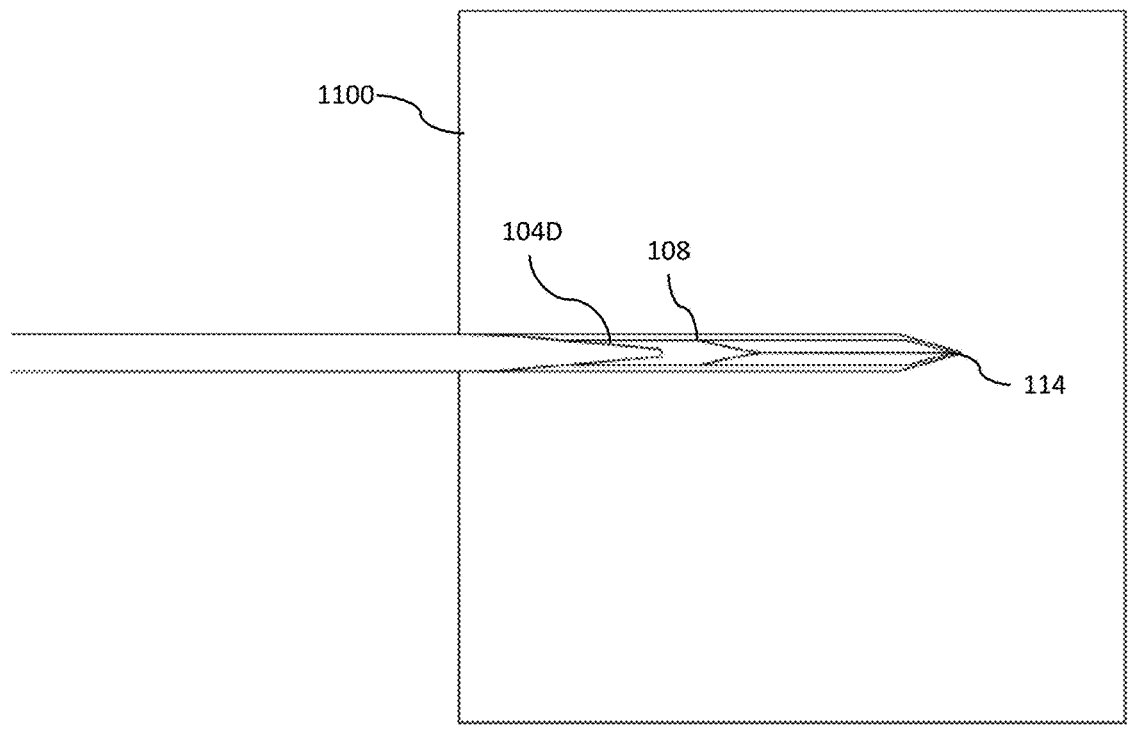

Now referring to FIG. 13, it can be seen that the blade edge 114 has cut deeper into the bone 1100 and the tapered portions 104D (and 104C, not shown) is inserted further into the cut portion of the bone 1100. Since the tapered portions 104D (and 104C, not shown) are further inserted into the bone 1100, they can carry more of the load of the bone 1100. FIG. 14 shows all of the blade extending into the bone 1100. As a result, load is transferred to the rails from the blade to allow for deeper and more efficient cutting since the blade will not bind under the pre-stress of the interface.

FIG. 15 illustrates a top view of the static casing 104 and the cutting end 106 having an internal fluid channel 1500 in accordance with embodiments of the present disclosure. The static casing 104 and the cutting end 106 are similar to the static casing 104 and the cutting end 106 shown in FIGS. 4, 5, 6, and 7 except for the inclusion of the internal fluid channel 1500 defined within the ultrasonic horn 108. Referring to FIG. 15, the channel may extend from one end 1502 where it is connected to a source of cooling fluid to an opening 1504 where the fluid may exit. After exiting the opening 1504, the cooling fluid may generally flow in the direction indicated by arrows 1506 over the top side of and around the ultrasonic horn 108. The cooling fluid may thereby cool the cutting end 106 and/or biological tissue that the cutting end 106 is transforming.

FIG. 16A illustrates a top view of the static casing 104 and the cutting end 106 having multiple internal fluid channels 1600 and 1602 within the side portions 104C and 104D, respectively, of the static casing 104 in accordance with embodiments of the present disclosure. The static casing 104 and the cutting end 106 are similar to the static casing 104 and the cutting end 106 shown in FIG. 15 except for the omission of the channel within the ultrasonic horn 106 and the inclusion of channels 1600 and 1602 within the side portions 104C and 104D. Referring to FIG. 16A, the channels 1600 and 1602 may extend from a respective end 1604 and 1606, respectively, where they are connected to a source of cooling fluid to openings 1608 and 1610, respectively, where the fluid may exit. After exiting the openings 1608 and 1610, the cooling fluid may generally flow in the direction indicated by arrows 1612 over the top side of and around the ultrasonic horn 108. The cooling fluid may thereby cool the cutting end 106 and/or biological tissue that the cutting end 106 is transforming.

FIG. 16B illustrates a top view of another static casing and cutting end having multiple internal fluid channels within the side portions of the static casing in accordance with embodiments of the present disclosure. Referring to FIG. 16B, the figure is similar to FIG. 16A but shows that coolant may flow in the space between the blade and the static casing. In this embodiment, no cannulations are needed. An external coolant, such as liquid nitrogen, may be used to provide direct conduction on the outside of the blade and internal to the casing.

FIGS. 17 and 18 illustrate top views of a cutting device 1700 in different positions in accordance with embodiments of the present disclosure. Referring to FIG. 17, the cutting device 1700 in a "neutral" position, meaning that the cutting end is not being moved by a mechanism (not shown) that is operatively attached to an opposing end. The cutting end 1702 includes a serrated portion 1704 for contacting and cutting biological tissue, such as bone, when the driving mechanism is activated. The mechanism for moving the cutting end may be any suitable driving mechanism that can create the desired motion. When the mechanism is activated, it can mechanically cause the cutting end 1702 to pivot back-and-forth in directions indicated by double arrow 1706. FIG. 18 shows the cutting end 1702 at a different position at the extent of its swing in one direction. The cutting end 1702 can also be moved similarly to a position in the other direction. The mechanism can move the cutting end 1702 rapidly back-and-forth such that it can cut biological tissue. It is noted that the rails 1708A and 1708B may be rigidly attached to a static housing similar to the other examples provided herein.

With continuing reference to FIGS. 17 and 18, the cutting device 1700 can include a static casing with side portions 1708A and 1708B having similar features and functions as the static casing side portions of the other cutting devices disclosed herein. In one way the side portions 1708A and 1708B differ from other static casing side portions disclosed herein in that the inner surfaces of the side portions 1710A and 1710B form a "V" shape to accommodate the back-and-forth swing of the cutting end 1702 during operation. Alternatively for example, the shape may be any other shape and dimension suitable for providing clearance for movement of the cutting device.

FIG. 19 illustrates a top view of a drilling device 1900 in accordance with embodiments of the present disclosure. Referring to FIG. 19, the device includes a static casing 1902 and drill bit 1904. An attached piezoelectric transducer may be operatively attached to an end (not shown) of a shank 1906 of the drill bit 1904 such that the transducer can ultrasonically rotate the drill bit 1904. During operation of the drill bit 1904, a cutting edge 1908 may be applied to bone or other biological tissue for removing a portion of the bone to create a hole in the bone.

With continuing reference to FIG. 19, the static casing includes side portions 1902A and 1902B that taper in the direction towards the cutting edge 1908. Similar to their use disclosed herein, the side portions 1902A and 1902B can receive load from the bone and reduce loading on the drill bit 1904. It is noted that the side portions 1902A and 1902B may be rigidly attached to a housing similar to the other examples provided herein. In this case, the housing is static relative to the motion of the drill bit 1904.

FIGS. 20A-20D illustrate a top perspective view and top views depicting some assembly of a cutting device 100 in accordance with embodiments of the present disclosure. Referring to FIGS. 20A-20D, it is shown that the casing is unique in that you can assemble the blade 108 through a casing that is already assembled to the housing.

FIGS. 21A-21C illustrate a top perspective view, a close-up perspective view, and a side view of an cutting device 108 having a cutting end with a raised blade edge 2100 in accordance with embodiments of the present disclosure. Referring to FIGS. 21A-21C, the edge of the blade edge 2100 is raised so that the bone to blade contact area is reduced even further, thus reducing the heat transfer between the designs. In this example, the blade edge 2100 is a saw type but may alternatively be any other suitable type of blade edge.

FIGS. 22A-22G illustrate a front view, a rear view, a top view, a bottom view, a side view, a top perspective view, and an exploded view, respectively, of a cutting device 2200 in accordance with embodiments of the present disclosure. Referring to FIGS. 22A-22G, it is noted that the cutting device is in some ways similar to the cutting device shown in FIG. 1; however, the side portions are shorter and the casing covers a portion of the working surface of the blade. Like reference numbers are used for like components for the cutting device 100 of FIG. 1 and the cutting device 2200 of FIGS. 22A-22G. This can provide the benefits of decoupling motion (longitudinally in this case), providing a slight relief for debris, and preventing heat transfer.

It is noted that embodiments of the present disclosure are described as producing or having ultrasonic movement produced by a piezoelectric transducer. It is noted that in the alternative the movement may be any suitable type of movement produced by any suitable source. Further, cutting may be applied to any suitable material or technical field. Suitable mechanical sources could include anything from piezoceramics, electro-mechanical motors, user generated hand motion, etc. However, its important to note that all types of mechanisms can produce equivalent types of movements. These could include, but are not limited to, axial motion, bending motion, torsional motion, flexural motion, etc. It is also feasible that the source of mechanical motion can combine all of these modes of motion to create more complex movements. Regardless of the motion and/or the manner in which it is produced, there would be a resultant motion at the end of the functional device/blade edge. This motion would, under the claims of this patent, be captured within the bounds of the static casing/rails which function to share load, decouple motion, and prevent heat transfer to the functional working surfaces. Examples include oscillating/sagittal/reciprocating medical bone cutting saws, medical rotary drills, medical rotary burs, construction hammer drills, construction rotary hammer, wood cutting axes, construction oscillating multi-tools, oscillating medical cast saws, cutting saws, etc. The principles of the claims presented in this patent could be applied to all of these devices with equivalently realized benefits.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A cutting device comprising:
   a static casing that defines a sheathing slot and an opening, wherein the sheathing slot extends to the opening and has a first height at an end of the opening;
   a horn including a first end and a second end, wherein the second end opposes the first end and includes a cutting component having a second height, wherein the first height is greater than the second height, and wherein the cutting component is positioned outside the opening; and
   a transducer being rigidly connected to the static casing, wherein the transducer is configured to generate vibrations to the first end of the horn for propagating movement to the second end of the horn with respect to the static casing and within the static casing.

2. The cutting device of claim 1, wherein the cutting component comprises a curved cutting portion.

3. The cutting device of claim 1, wherein the cutting component comprises a serrated portion.

4. The cutting device of claim 1, wherein the static casing and the horn are separated by a plurality of gaps.

5. The cutting device of claim 1, wherein the second end of the horn extends beyond the sheathing slot of the static casing.

6. The cutting device of claim 1, wherein the static casing defines a channel in its interior and another opening positioned proximate the horn for passage of a fluid to the horn.

7. The cutting device of claim 1, wherein the horn defines a channel in its interior and another opening positioned proximate the second end of the horn for passage of a fluid.

8. The cutting device of claim 1, wherein the propagated movement comprises ultrasonic movement.

9. A method of using a cutting device, the method comprising:
providing the cutting device comprising
a static casing that defines a sheathing slot and an opening, wherein the sheathing slot extends to the opening and has a first height at an end of the opening;
a horn including a first end and a second end, wherein the second end opposes the first end and includes a cutting component having a second height, wherein the first height is greater than the second height, and wherein the cutting component is positioned outside the opening;
a transducer being rigidly connected to the static casing, wherein the transducer is configured to generate vibrations to the first end of the horn for propagating movement to the second end of the horn with respect to the static casing and within the static casing; and
activating the transducer for generating the vibrations.

10. The method of claim 9, wherein the cutting component comprises a curved cutting portion.

11. The method of claim 9, wherein the cutting component comprises a serrated portion.

12. The method of claim 9, wherein the static casing and the horn are separated by a plurality of gaps.

13. The method of claim 9, wherein the second end of the horn extends beyond the sheathing slot of the static casing.

14. The method of claim 9, wherein the static casing defines a channel in its interior and another opening positioned proximate the horn for passage of a fluid to the horn.

15. The method of claim 9, wherein the horn defines a channel in its interior and another opening positioned proximate the second end of the horn for passage of a fluid.

16. The method of claim 9, wherein the propagated movement comprises ultrasonic movement.

* * * * *